(12) United States Patent
Davies

(10) Patent No.: US 9,042,977 B2
(45) Date of Patent: *May 26, 2015

(54) METHOD AND SYSTEM FOR DETECTING ELECTROPHYSIOLOGICAL CHANGES IN PRE-CANCEROUS AND CANCEROUS BREAST TISSUE AND EPITHELIUM

(75) Inventor: Richard J. Davies, Saddle River, NJ (US)

(73) Assignee: Epi-Sci, LLC, Saddle River, NJ (US)

( * ) Notice: Subject to any disclaimer, the term of this patent is extended or adjusted under 35 U.S.C. 154(b) by 259 days.

This patent is subject to a terminal disclaimer.

(21) Appl. No.: 13/600,526

(22) Filed: Aug. 31, 2012

(65) Prior Publication Data
US 2012/0323137 A1 Dec. 20, 2012

Related U.S. Application Data

(60) Continuation of application No. 12/589,434, filed on Oct. 23, 2009, now Pat. No. 8,275,453, which is a division of application No. 10/717,074, filed on Nov. 19, 2003, now Pat. No. 7,630,759, which is a continuation-in-part of application No. 10/151,233, filed on May 20, 2002, now Pat. No. 6,922,586.

(51) Int. Cl.
*A61B 5/05* (2006.01)
*A61B 5/053* (2006.01)
(Continued)

(52) U.S. Cl.
CPC .......... *A61B 5/0531* (2013.01); *A61B 5/04002* (2013.01); *A61B 5/04082* (2013.01); *A61B 5/4312* (2013.01); *A61B 5/4839* (2013.01)

(58) Field of Classification Search
USPC ......... 600/547, 382, 386, 442, 506, 536, 554, 600/562, 573, 511, 376, 439, 483, 549, 600/513; 606/32, 34, 41; 601/2; 324/600; 604/20; 424/764; 514/2, 53, 23, 54, 58, 514/60; 435/183, 69.1, 320.1, 325
See application file for complete search history.

(56) References Cited

U.S. PATENT DOCUMENTS

| | | |
|---|---|---|
| 3,786,801 A | 1/1974 | Sartorius |
| 3,949,736 A | 4/1976 | Vrana et al. |

(Continued)

FOREIGN PATENT DOCUMENTS

| | | |
|---|---|---|
| DE | 2208653 B1 | 4/1973 |
| WO | 98/23204 A1 | 6/1998 |

(Continued)

OTHER PUBLICATIONS

Foster KR, Schwan HP. Dielectric Properties of Tissues and Biological Materials: A Critical Review. Critical Reviews in Biomedical Engineering, 1989, pp. 25-104 vol. 17, Issue 1, CRC Press, England.

(Continued)

*Primary Examiner* — Brian Szmal
(74) *Attorney, Agent, or Firm* — Lerner, David, Littenberg, Krumholz & Mentlik, LLP

(57) ABSTRACT

A method and system are provided for determining a condition of a selected region of epithelial and stromal tissue in the human breast. A plurality of measuring electrodes are used to measure the tissue and transepithelial electropotential of breast tissue. Surface electropotential and impedance are also measured at one or more locations. An agent may be introduced into the region of tissue to enhance electrophysiological characteristics. The condition of the tissue is determined based on the electropotential and impedance profile at different depths of the epithelium, stroma, tissue, or organ, together with an estimate of the functional changes in the epithelium due to altered ion transport and electrophysiological properties of the tissue. Devices for practicing the disclosed methods are also provided.

11 Claims, 11 Drawing Sheets

(51) Int. Cl.
*A61B 5/04* (2006.01)
*A61B 5/0408* (2006.01)
*A61B 5/00* (2006.01)

(56) References Cited

U.S. PATENT DOCUMENTS

| | | |
|---|---|---|
| 4,291,708 A | 9/1981 | Frei et al. |
| 4,458,694 A | 7/1984 | Sollish et al. |
| 4,486,835 A | 12/1984 | Bai et al. |
| 4,690,152 A | 9/1987 | Juncosa |
| 4,729,385 A | 3/1988 | Juncosa et al. |
| 4,955,383 A | 9/1990 | Faupel |
| 5,099,844 A | 3/1992 | Faupel |
| 5,109,849 A | 5/1992 | Goodman et al. |
| 5,143,079 A | 9/1992 | Frei et al. |
| 5,345,935 A | 9/1994 | Hirsch et al. |
| 5,415,164 A | 5/1995 | Faupel et al. |
| 5,417,222 A | 5/1995 | Dempsey et al. |
| 5,639,444 A | 6/1997 | Klaveness |
| 5,678,547 A | 10/1997 | Faupel et al. |
| 5,697,369 A | 12/1997 | Long, Jr. et al. |
| 5,722,404 A | 3/1998 | Lundback |
| 5,766,165 A | 6/1998 | Gentelia et al. |
| 5,810,742 A | 9/1998 | Pearlman |
| 5,823,957 A | 10/1998 | Faupel et al. |
| 5,833,622 A | 11/1998 | Meathrel et al. |
| 5,906,208 A | 5/1999 | Ishikawa |
| 6,026,322 A | 2/2000 | Korenman et al. |
| 6,122,544 A | 9/2000 | Organ |
| 6,134,480 A | 10/2000 | Minogue et al. |
| 6,135,953 A | 10/2000 | Carim |
| 6,138,044 A | 10/2000 | Svedman |
| 6,148,232 A | 11/2000 | Avrahami et al. |
| 6,251,681 B1 | 6/2001 | Davies et al. |
| 6,308,097 B1 | 10/2001 | Pearlman |
| 6,312,428 B1 | 11/2001 | Eggers et al. |
| 6,314,315 B1 | 11/2001 | Hung |
| 6,328,735 B1 | 12/2001 | Curley et al. |
| 6,351,666 B1 | 2/2002 | Cuzick et al. |
| 6,363,275 B1 | 3/2002 | Kaiser |
| 6,366,795 B1 | 4/2002 | Bremer et al. |
| 6,389,305 B1 | 5/2002 | Deban et al. |
| 6,391,026 B1 | 5/2002 | Hung et al. |
| 6,456,865 B2 | 9/2002 | Samson |
| 6,471,660 B1 | 10/2002 | Covington |
| 6,496,725 B2 | 12/2002 | Kamada et al. |
| 6,500,173 B2 | 12/2002 | Underwood et al. |
| 6,641,604 B1 | 11/2003 | Adelman et al. |
| 6,712,816 B2 | 3/2004 | Hung et al. |
| 6,773,418 B1 | 8/2004 | Sharrow et al. |
| 6,823,203 B2 | 11/2004 | Jordan |
| 6,842,264 B1 | 1/2005 | Leyva et al. |
| 6,887,239 B2 | 5/2005 | Elstrom et al. |
| 6,898,303 B2 | 5/2005 | Armato, III et al. |
| 6,922,586 B2 | 7/2005 | Davies |
| 6,993,383 B2 | 1/2006 | Assenheimer et al. |
| 7,077,842 B1 | 7/2006 | Cosman |
| 7,223,239 B2 | 5/2007 | Schulze et al. |
| 7,499,745 B2 | 3/2009 | Littrup et al. |
| 7,630,759 B2 * | 12/2009 | Davies .................. 600/547 |
| 2001/0051774 A1 | 12/2001 | Littrup et al. |
| 2002/0006216 A1 | 1/2002 | Armato et al. |
| 2002/0026123 A1 | 2/2002 | Pearlman |
| 2002/0110609 A1 | 8/2002 | Hung |
| 2002/0133151 A1 | 9/2002 | Hung et al. |
| 2002/0183645 A1 | 12/2002 | Nachaliel |
| 2002/0188187 A1 | 12/2002 | Jordan |
| 2003/0010987 A1 | 1/2003 | Banin et al. |
| 2003/0040734 A1 | 2/2003 | Morton et al. |
| 2003/0088189 A1 | 5/2003 | Tu et al. |
| 2003/0109871 A1 | 6/2003 | Johnson et al. |
| 2003/0170840 A1 | 9/2003 | McDonald et al. |
| 2003/0187366 A1 | 10/2003 | Hashimshony |
| 2003/0216661 A1 | 11/2003 | Davies |
| 2004/0133122 A1 | 7/2004 | Pearlman |
| 2004/0152997 A1 | 8/2004 | Davies |
| 2004/0253652 A1 | 12/2004 | Davies |
| 2005/0059928 A1 | 3/2005 | Larsson |
| 2005/0203436 A1 | 9/2005 | Davies |

FOREIGN PATENT DOCUMENTS

| | | |
|---|---|---|
| WO | 9923945 | 5/1999 |
| WO | 0035357 | 6/2000 |
| WO | 0143630 A2 | 6/2001 |
| WO | 0232335 | 4/2002 |

OTHER PUBLICATIONS

Emtestam L, Ollmar S. Electrical Impedance Index in Human Skin: Measurements After Occlusion, In 5 Anatomical Regions and in Mild Irritant Contact Dermatitis. Contact Dermatitis Environmental and Occupational Dermatitis, Feb. 1993, pp. 104-108, vol. 28, No. 2, RJG Rycroft, London, England.

Ollmar S, Eek A, Sundstrom F, Emtestam L. Electrical Impedance for Estimation of Irritation in Oral Mucosa and Skin. Medical Progress Technology, Feb. 1995, pp. 29-37, vol. 21. No. 1, Kluwer Academic Publishers.

Ollmar S, Nyren M, Nicander I, Emtestam L. Electrical Impedance Compared With Other Non-Invasive Bioengineering Techniques and Visual Scoring for Detection of Irritation in Human Skin, British Journal of Dermatology, Jan. 1994, pp. 29-36, vol. 130, No. 1, Blackwell Scientific Publications.

Nicander I, Ollmar S, Rozell BL, Eek A, Emtestam L. Electrical Impedance Measureed to Five Skin Depths in Mild Irritant Dermatitis Induced by Sodium Lauryl Sulphate, British Journal of Dermatology, May 1995, pp. 718-724, vol. 132, No. 5, Blackwell Scientific Publications.

Kristt D, Winston GJ, Mellov MM, Veltman V, Koren R. Patterns of Proliferative Changes in Crypts Bordering Colonic Tumors: Zonal Histology and Cell Cycle Marker Expression. Pathology Oncology Research, 1999; pp. 297-303, vol. 5, No. 4.

Lackermeier AH, McAdams ET, Moss GP, Woolfson AD. In Vivo Ac Impedance Spectroscopy of Human Skin. Theory and Problems in Monitoring of Passive Percutaneous Drug Delivery. Annals of the New York Academy of Sciences, 1999, pp. 197-213, vol. 873.

Cuzick J, Holland R, Barth V, Davies R, Faupel M, Fentiman I et al. Electropotential Measurements as a New Diagnostic Modality for Breast Cancer. The Lancet, Aug. 1998, pp. 359-363, vol. 352, No. 9125.

Faupel M, Vanel D, Barth V, Davies R, Fentiman IS, Holland R et al. Electropotential Evaluation as a New Technique for Diagnosing Breast Lesions. European Journal of Radiology, Jan. 1997, pp. 33-38. vol. 24, No. 1, Elsevier.

Hülser DF, Frank W. Stimulation of Embryonic Rat Cell in Culture by a Protein Fraction Isolated From Fetal Calf Serum, Publishing House of the Periodical for Nature Research, Jul. 1971, pp. 1045-1048, vol. 26b, No. 7.

Moolenaar WH, De Laat SW, Van Der Saag PT. Serum Triggers a Sequence of Rapid Ionic Conductance Changes in Quiescent Neuroblastoma Cells, Nature, Jun. 14, 1979, pp. 721-723, vol. 279, No. 5714.

Reuss L, Cassel D, Rothenberg P, Whiteley P, Mancuso D, Glaser L. Mitogens and Ion Fluxes. In: Mandel LJ, Benos DJ, Editors. The Role of Membranes in Cell Growth and Differentiation, Academic Press Inc., Hartcourt Brace Jovanovich, 1986, pp. 3-54, vol. 27, Orlando, Fla.

Moolenaar WH, De Laat SW, Mummery CL, Van Der Saag PT. Na+/H+ Exchange in the Action of Growth Factors. In: Boynton AL, McKeehan WL, Whitfield JF, editors. Ions, Cell Proliferation and Cancer, Academic Press, Inc., 1982, pp. 151-162, New York.

Rothenberg P, Reuss L, Glaser L. Serum and Epidermal Growth Factor Transiently Depolarize Quiescent BSC-1 Epithelial Cells, Proceedings of the National Academy of Sciences of the United States of America, Dec. 1982, pp. 7783-7787, vol. 79, No. 24.

Schultz SG. Homocellular Regulatory Mechanisms in Sodium-Transporting Epithelia: Avoidance of Extinction by "Flush-Through", American Journal of Physiology, Dec. 1981, pp. F579-F590, vol. 241, No. 6, The American Physiological Society.

(56) References Cited

OTHER PUBLICATIONS

Boonstra J, Moolenaar WH, Harrison PH, Moed P, Van Der Saag PT, De Laat SW. Ionic Responses and Growth Stimulation Induced by Nerve Growth Factor and Epidermal Growth Factor in Rat Pheochromocytoma (PC12) cells, The Journal of Cell Biology, Jul. 1983, pp. 92-98, vol. 97, No. 1, The Rockefeller University Press.
Redmann K, Walliser S. Different Changes in Transmembrane Potential of Cultured Cells After Ouabain-Inhibited Active Na+/K+-Transport. Archiv Fur Geschwulstforsch, 1981; pp. 96-102. vol. 51, No. 1, Volk and Gesundheit, Berlin.
Prat AG, Cunningham CC, Jackson GR, Jr., Borkan SC, Wang Y, Ausiello DA et al. Actin Filament Organization is Required for Proper Camp-Dependent Activation of CFTR., American Journal of Physiology, Dec. 1999, pp. C1160-C1169 vol. 277, No. 6 Part 1, The American Physiology Society.
Rouzaire-Dubois B, Milandri JB, Bostel S, Dubois JM. Control of Cell Proliferation by Cell Volume Alterations in Rat C6 Glioma Cells. Pflugers Archiv European Journal of Physiology, Oct. 2000, vol. 440, No. 6, Springer.
Ernst M, Adam G. Regulation of Passive Potassium Transport of Normal and Transformed 3T3 Mouse Cell Cultures by External Calcium Concentration and Temperature. Journal of Member Biology, 1981; pp. 155-172, vol. 61, No. 3, Springer-Verlag New York Inc.
Diserbo M, Fatome M, Verdetti J. Activation of Large Conductance Ca(2+)-Activated K+ Channels in N1E-115 Neuroblastoma Cells by Platelet-Activating Factor. Biochemical and Biophysical Research Community, Jan. 1996, pp. 745-749, vol. 218, No. 3, Academic Press.
Rane SG. A Ca2(+)-Activated K+ Current in Ras-Transformed Fibroblasts is Absent From Nontransformed Cells, American Journal of Physiology, Jan. 1991, pp. C104-C112, vol. 260, No. 1, Part 1, The American Physiological Society.
Sachs HG, Stambrook PJ, Ebert JD. Changes in Membrane Potential During the Cell Cycle, Experimental Cell Research, Feb. 1974, pp. 362-366, vol. 83, No. 2, Academic Press, New York and London.
Kiefer H, Blume AJ, Kaback HR. Membrane Potential Changes During Mitogenic Stimulation of Mouse Spleen Lymphocytes, Proceedings of the National Academy of Sciences, of the United States of America, Apr. 1980, pp. 2200-2204, vol. 77, No. 4.
Moolenaar WH, Mummery CL, Van Der Saag PT, De Laat SW. Rapid Ionic Events and the Initiation of Growth in Serum-Stimulated Neuroblastoma Cells, Cell Mar. 1981, pp. 789-798, vol. 23, No. 3.
Chapman LM, Wondergem R. Transmembrane Potential and Intracellular Potassium Ion Activity in Fetal and Maternal Liver, Journal of Cellular Physiology, Oct. 1984, pp. 7-12, vol. 121, No. 1, Alan R. Liss, Inc.
Decoursey TE, Cherny VV. Voltage-Activated Proton Currents in Human THP-1 Monocytes, The Journal of Membrane Biology, Jul. 1996, pp. 131-140, vol. 152, No. 2, Springer.
Kapural L, Fein A. Changes in the Expression of Voltage-Gated K+ Currents During Development of Human Megakaryocytic Cells, Biochimica et Biophysica Acta 1997, pp. 319-328; vol. 1326, No. 2, Elsevier, USA.
Wieland SJ, Chou RH, Chen TA. Elevation of a Potassium Current in Differentiating Human Leukemic (HI-60) Cells, Journal of Cell Physiology, Aug. 1987, pp. 371-375, vol. 132, No, 2, Alan R. Liss, Inc.
Simonneau M, Distasi C, Tauc L, Poujeoi C. Development of Ionic Channels During Mouse Neuronal Differentiation, Journal de Physiologie, 1985, pp. 312-332, vol. 80, No. 2, Masson, Paris, France.
Veselovskii NS, Fomina AF. [Sodium and Calcium Channels of the Somatic Membrane of Neuroblastoma Cells During Artificially Induced Differentiation]. Neirofiziologiia 1986; pp. 207-214, vol. 18, No. 2.
Vyklicky L, Jr., Michl J, Vlachova V, Vyklicky L, Vyskocil F. Ionic Currents in Neuroblastoma Clone E-7 Cells, Neuroscience Letters, 1985, pp. 197-201, vol. 55, No. 2, Elsevier Scientific Publishers, Ireland.
Felber SM, Brand MD. Concanavalin A Causes an Increase in Sodium Permeability and Intracellular Sodium Content of Pig Lymphocytes, The Biochemical Journal, Mar. 1983, pp. 893-897, vol. 210, No. 3, The Biochemical Society, London.
O'Donnell ME, Villereal ML. Membrane Potential and Sodium Flux in Neuroblastoma X Glioma Hybrid Cells: Effects of Amiloride and Serum, Journal of Cellular Physiology, Dec. 1982, pp. 405-412, vol. 113, No. 3, Alan R. Liss, Inc.
Leffert HL, Koch KS. Ionic Events At the Membrane Initiate Rat Liver Regeneration. Ann The New York Academy of Sciences, 1980, pp. 201-215, vol. 339, New York, USA.
Villereal ML. Sodium Fluxes in Human Fibroblasts: Effect of Serum, Ca+2, and Amiloride. Journal of Cellular Physiology, Jun. 1981, pp. 359-369, vol. 107, No. 3, Alan R. Liss, Inc.
Fehlmann M, Canivet B, Freychet P. Epidermal Growth Factor Stimulates Monovalent Cation Transport in Isolated Rat Hepatocytes, Biochemical and Biophysical Research Communications, May 1981, pp. 254-260, vol. 100, No. 1, Academic Press Inc.
Moolenaar WH, Tsien RY, Van Der Saag PT, De Laat SW. Na+/H+ Exchange and Cytoplasmic Ph in the Action of Growth Factors in Human Fibroblasts. Nature, International Weekly Journal of Science, Aug. 1983, pp. 645-648, vol. 304, No. 5927, MacMillan Journals, Ltd.
Paris S, Pouyssegur J. Biochemical Characterization of the Amiloride-Sensitive Na+/H+ Antiport in Chinese Hamster Lung Fibroblasts, The Journal of Biological Chemistry, Mar. 1983, pp. 3503-3508, vol. 258, No. 6, The American Society of Biological Chemists, Inc., USA.
Paris S, Pouyssegur J. Growth Factors Activate the Na+/H+ Antiporter in Quiescent Fibroblasts by Increasing Its Affinity for Intracellular H+, The Journal of Biological Chemistry, Sep. 1984, pp. 10989-10994, vol. 259, No. 17, The American Society of Biological Chemists, Inc., USA.
Pouyssegur J, Chambard JC, Franchi A, Paris S, Obberghen-Schilling E. Growth Factor Activation of an Amiloride-Sensitive Na+/H+ Exchange System in Quiescent Fibroblasts: Coupling to Ribosomal Protein S6 Phosphorylation, Proceedings of the National Academy of Sciences of the United States of America, Jul. 1982, pp. 3935-3939, vol. 79, No. 13, National Academy of Sciences, USA.
Pouyssegur J, Sardet C, Franchi A, L'Allemain G, Paris S. A Specific Mutation Abolishing Na+/H+ Antiport Activity in Hamster Fibroblasts Precludes Growth At Neutral and Acidic Ph., Proceedings of the National Academy of Sciences of the United States of America, Aug. 1984, pp. 4833-4837, vol. 81, No. 15, National Academy of Sciences, USA.
Moolenaar WH, Tertoolen LG, De Laat SW. The Regulation of Cytoplasmic pH in Human Fibroblasts, The Journal of Biological Chemistry. Jun. 1984, pp. 7563-7569, vol. 259, No. 12, The American Society of Biological Chemists, Inc., USA.
Deutsch C, Price M. Role of Extracellular Na and K in Lymphocyte Activation, Journal of Cellular Physiology, Oct. 1982, pp. 73-79, vol. 113, No. 1, Alan R. Liss, Inc.
Saqr HE, Guan Z, Yates AJ, Stokes BT. Mechanisms Through Which PDGF Alters Intracellular Calcium Levels in U-1242 MG Human Glioma Cells, Neurochemistry International, Dec. 1999, pp. 411-422, vol. 35, No. 6, Elsevier Science Ltd.
Chen CF, Corbley MJ, Roberts TM, Hess P. Voltage-Sensitive Calcium Channels in Normal and Transformed 3T3 Fibroblasts, Science, Feb. 1988, pp. 1024-1026, vol. 239, No. 4843.
Owen NE, Villereal ML. Role of Ca2+ in Serum-Stimulated Na+ Influx in Normal and Transformed Cells, American Journal of Physiology, Mar. 1985, pp. C288-C295, vol. 248, No. 3 Pt 1, The American Physiological Society.
Macara IG. Oncogenes, ions, and Phospholipids, American Journal of Physiology, Jan. 1985, pp. C3-C11, vol. 248, No. 1 Pt 1, The American Physiological Society.
Cameron IL, Smith NK, Pool TB, Sparks RL. Intracellular Concentration of Sodium and Other Elements as Related to Mitogenesis and Oncogenesis In Vivo, Cancer Research, May 1980, pp. 1493-1500, vol. 40, No. 5.
Goller DA, Weidema WF, Davies RJ. Transmural Electrical Potential Difference as an Early Marker in Colon Cancer. Archives of Surgery, Mar. 1986, pp. 345-350, vol. 121, No. 3, The American Medical Association, USA.

(56) References Cited

OTHER PUBLICATIONS

Davies RJ, Weidema WF, Sandle GI, Palmer L, Deschner EE, Decosse JJ. Sodium Transport in a Mouse Model of Colonic Carcinogenesis, Cancer Research, Sep. 1987, pp. 4646-4650, vol. 47, No. 17.

Davies RJ, Juncosa RD, Kaplan D, Pempinello C, Asbun H, Pilch YH. Colonic Epithelial Impedance Analysis in a Murine Model of Large-Bowel Cancer, Archives of Surgery, Nov. 1986, pp. 1253-1258, vol. 121, No. 11, The American Medical Association, USA.

Davies RJ, Joseph R, Kaplan D, Juncosa RD, Pempinello C, Asbun H et al. Epithelial Impedance Analysis in Experimentally Induced Colon Cancer, Biophysical Journal, Nov. 1987, pp. 783-790, vol. 52, No. 5, The Biophysical Society by The Rockefeller University Press, USA.

Davies RJ, Joseph R, Asbun H, Sedwitz M. Detection of the Cancer-Prone Colon, Using Transepithelial Impedance Analysis, Archives of Surgery, Apr. 1989, pp. 480-484, vol. 124, No. 4, The American Medical Association, USA.

Schaefer H, Schanne O. Membranpotentiale Von Einzelzellen in Gewebekulturen, Naturwissenschaften 1956, p. 445, vol. 43, Springer-Verlag.

Tokuoka S, Morioka H. The Membrane Potential of the Human Cancer and Related Cells, "GANN" The Japanese Journal of Cancer Research, Gann, 1957, pp. 353-354, vol. 48, The Japanese Cancer Association and the Japanese Foundation for Cancer Research, Nishi-Sugamo, Toshima-ku, Tokyo, Japan.

Balitsky KP, Shuba EP. Resting Potential of Malignant Cells, ACTA, Eighth International Cancer Congress, 1964, pp. 1391-1393, vol. 20, No. 67.

Cone CD, Jr. Unified Theory on the Basic Mechanism of Normal Mitotic Control and Oncogenesis, Journal of Theoretical Biology, Jan. 1971, pp. 151-181, vol. 30, No. 1, Academic Press.

Cone CD, Jr., Cone CM. Induction of Mitosis in Mature Neurons in Central Nervous System by Sustained Depolarization, Science, Apr. 1976, pp. 155-158, vol. 192, No. 4235.

Cone CD, Jr. The Role of the Surface Electrical Transmembrane Potential in Normal and Malignant Mitogenesis, Annals of the New York Academy of Sciences, 1974, pp. 420-435, vol. 238, The New York Academy of Sciences, USA.

Lai CN, Gallick GE, Arlinghaus RB, Becker FF. Temperature-Dependent Transmembrane Potential Changes in Cells Infected With a Temperature-Sensitive Moloney Sarcoma Virus, Journal of Cellular Physiology, Oct. 1984, pp. 139-142, vol. 121, No. 1, Alan R. Liss, Inc.

Binggeli R, Cameron IL. Cellular Potentials of Normal and Cancerous Fibroblasts and Hepatocytes, Cancer Research, Jun. 1980, pp. 1830-1835, vol. 40, No. 6.

Koch KS, Leffert HL. Growth Control of Differentiated Adult Rat Hepatocytes in Primary Culture, Annals of the New York Academy of Sciences, 1980, pp. 111-127, vol. 349, The New York Academy of Sciences, New York, USA.

Funkhouser WK, Pilch YH, Davies RJ. The Electrophysiologic Changes Associated with Premalignancy in Colon Carcinogenesis, Federation Proceedings, Mar. 1986, p. 742, vol. 45, No. 4, Federation of American Societies for Experimental Biology.

Huang Y, Rane SG. Single Channel Study of a Ca(2+)-Activated K+ Current Associated With Ras-Induced Cell Transformation, The Journal of Physiological Society, 1993, pp. 601-618, vol. 461, Cambridge University Press.

Davies RJ, Weiss A, Capko D, Brenner BM. Cell Membrane Potential in Benign and Malignant Breast Epithelial Cells. Breast Cancer Research and Treatment, 1996, p. 331, vol. 41, No. 3 Ref Type: Abstract, Kluwer Academic Publishers.

Schultz SG. Basic Principles of Membrane Transport, 1 ed. 1980, Cambridge University Press, London and New York.

Nagy IZ, Lustyik G, Nagy VZ, Zarandi B, Bertoni-Freddari C. Intracellular Na+:K+ Ratios in Human Cancer Cells as Revealed by Energy Dispersive X-Ray Microanalysis, The Journal of Cell Biology, Sep. 1981, pp. 769-777, vol. 90, No. 3, The Rockefeller University Press, USA.

Bustin SA, Li SR, Dorudi S. Expression of the Ca2+-Activated Chloride Channel Genes CLCA1 and CLCA2 is Downregulated in Human Colorectal Cancer, DNA and Cell Biology, Nov. 2001, pp. 331-338, vol. 20, No. 6, Mary Ann Liebert, Inc., London, U.K.

Broaddus RR, Wargovich MJ, Castro GA. Early stages of 1,2-dimethylhydrazine-Induced Colon Carcinogenesis Suppress Immune-Regulated Ion Transport of Mouse Distal Colon, Cancer Research, Nov. 1994, pp. 5930-5936, vol. 54, No. 22, Official Journal of the American Association for Cancer Research, USA.

Morris AP, Cunningham SA, Benos DJ, Frizzell RA. Cellular Differentiation is Required for cAMP but Not Ca(2+)-dependent Cl-Secretion in Colonic Epithelial Cells Expressing High Levels of Cystic Fibrosis Transmembrane Conductance Regulator, The Journal of Biological Chemistry, Mar. 1992, pp. 5575-5583, vol. 267, No. 8, The American Society for Biochemistry and Molecular Biology.

Champigny G, Verrier B, Lazdunski M. A Voltage, Calcium, and ATP Sensitive Non Selective Cation Channel in Human Colonic Tumor Cells, Biochemical and Biophysical Research Communications, May 1991, pp. 1196-1203, vol. 176, No. 3, Academic Press, Inc.

Yao X, Kwan HY. Activity of Voltage-Gated K+ Channels is Associated With Cell Proliferation and Ca2+ Influx in Carcinoma Cells of Colon Cancer, Life Sciences Including Pharmacology Letters, May 1999, pp. 55-62, vol. 65, No. 1, Elsevier Science, Inc.

Wissenbach U, Niemeyer BA, Fixemer T, Schneidewind A, Trost C, Cavalie A et al. Expression of CaT-like, A Novel Calcium-Selective Channel, Correlates With the Malignancy of Prostate Cancer, The Journal of Biological Chemistry, Jun. 2001, pp. 19461-19468, vol. 276, No. 22, The American Society for Biochemistry and Molecular Biology.

Niemeyer BA, Bergs C, Wissenbach U, Flockerzi V, Trost C. Competitive Regulation of CaT-Like Mediated Ca2+ Entry by Protein Kinase C and Calmodulin, Proceedings of the National Academy of Sciences of the United States of America, Mar. 2001, pp. 3600-3605, vol. 98, No. 6.

Laniado ME, Fraser SP, Djamgoz MB. Voltage-Gated K(+) Channel Activity in Human Prostate Cancer Cell Lines of Markedly Different Metastatic Potential: Distinguishing Characteristics of PC-3 and LNCaP cells, The Prostate, 2001, pp. 262-274, vol. 46, No. 4, Wiley-Liss, Inc.

Shuba YM, Prevarskaya N, Lemonnier L, Van Coppenolle F, Kostyuk PG, Mauroy B et al. Volume-Regulated Chloride Conductance in the LNCaP Human Prostate Cancer Cell Line, American Journal of Physiology Cell Physiology, Oct. 2000, pp. C1144-C1154, vol. 279, No. 4, The American Physiological Society.

Fraser SP, Grimes JA, Djamgoz MB. Effects of Voltage-Gated Ion Channel Modulators on Rat Prostatic Cancer Cell Proliferation: Comparison of Strongly and Weakly Metastatic Cell Lines, The Prostate, 2000, pp. 61-76, vol. 44, No. 1, Wiley-Liss, Inc.

Rane SG. The Growth Regulatory Fibroblast IK Channel is the Prominent Electrophysiological Feature of Rat Prostatic Cancer Cells, Biochemical and Biophysical Research Communications, Mar. 2000, pp. 457-463, vol. 269, No. 2, Academic Press.

Skryma R, Van Coppenolle F, Dufy-Barbe L, Dufy B, Prevarskaya N. Characterization of Ca(2+)-Inhibited Potassium Channels in the LNCaP Human Prostate Cancer Cell Line, Receptors and Channels, 1999, pp. 241-253, vol. 6, No. 4, Harwood Academic Publishers, Malaysia.

Diss JK, Stewart D, Fraser SP, Black JA, Dib-Hajj S, Waxman SG et al. Expression of Skeletal Muscle-Type Voltage-Gated Na+ Channel in Rat and Human Prostate Cancer Cell Lines, FEBS Letters, May 1998, pp. 5-10, vol. 427, No. 1, Elsevier on Behalf of the Federation of European Biochemical Sciences.

Grimes JA, Djamgoz MB. Electrophysiological Characterization of Voltage-Gated Na+ Current Expressed in the Highly Metastatic Mat-LyLu Cell Line of Rat Prostate Cancer, Journal of Cellular Physiology, Apr. 1998, pp. 50-58, vol. 175, No. 1, Wiley-Liss, Inc.

Skryma RN, Prevarskaya NB, Dufy-Barbe L, Odessa MF, Audin J, Dufy B. Potassium conductance in the Androgen-Sensitive Prostate Cancer Cell Line, LNCaP: Involvement in Cell Proliferation, The Prostate, 1997, pp. 112-122, vol. 33, No. 2, Wiley-Liss, Inc.

Laniado ME, Lalani EN, Fraser SP, Grimes JA, Bhangal G, Djamgoz MB et al. Expression and Functional Analysis of Voltage-Activated Na+ channels in Human Prostate Cancer Cell Lines and Their Con-

(56) References Cited

OTHER PUBLICATIONS tribution to Invasion In Vitro, The American Journal of Pathology, Apr. 1997, pp. 1213-1221, vol. 150, No. 4, American Society for Investigative Pathology.

Grimes JA, Fraser SP, Stephens GJ, Downing JE, Laniado ME, Foster CS et al. Differential Expression of Voltage-Activated Na+ currents in Two Prostatic Tumour Cell Lines: Contribution to Invasiveness In Vitro, FEBS Letters, Aug. 1995, pp. 290-294, vol. 369, No. 2-3, Elsevier on Behalf of the Federation of European Biochemical Societies.

Wykoff CC, Beasley N, Watson PH, Campo L, Chia SK, English R et al. Expression of the Hypoxia-Inducible and Tumor-Associated Carbonic Anhydrases in Ductal Carcinoma in Situ of the Breast, The American Journal of Pathology, Mar. 2001, pp. 1011-1019, vol. 158, No. 3, American Society for Investigative Pathology.

Stemmer-Rachamimov AO, Wiederhold T, Nielsen GP, James M, Pinney-Michalowski D, Roy JE et al. NHE-RF, A Merlin-Interacting Protein, is Primarily Expressed in Luminal Epithelia, Proliferative Endometrium, and Estrogen Receptor-Positive Breast Carcinomas, The American Journal of Pathology, Jan. 2001, pp. 57-62, vol. 158, No. 1, American Society for Investigative Pathology.

Klimatcheva E, Wonderlin WF. An ATP-Sensitive K(+) Current That Regulates Progression Through Early G1 Phase of the Cell Cycle in MCF-7 Human Breast Cancer Cells, The Journal of Membrane Biology, Sep. 1999, pp. 35-46, vol. 171, No. 1, Spinger.

Liu MP, Handschumacher RE. Tamoxifen Induces Na+-Dependent Uridine Transport and Dome Formation in a Human Breast Tumor Cell Line, The Cancer Journal from Scientific American, Aug. 1995, pp. 210-214, vol. 1, No. 3.

Shen MR, Droogmans G, Eggermont J, Voets T, Ellory JC, Nilius B. Differential expression of Volume-Regulated Anion Channels During Cell Cycle Progression of Human Cervical Cancer Cells, The Journal of Physiology, Dec. 2000, pp. 385-394, vol. 529, Pt 2, The Physiological Society.

Shen MR, Chou CY, Ellory JC. Volume-Sensitive KCl cotransport Associated With Human Cervical Carcinogenesis, Pflügers Archibe European Journal of Physiology, Sep. 2000, pp. 751-760, vol. 440, No. 5, Springer.

Chou CY, Shen MR, Wu SN. Volume-sensitive Chloride Channels Associated With Human Cervical Carcinogenesis, Cancer Research, Dec. 1995, pp. 6077-6083, vol. 55, No. 24, Official Journal of the American Association for Cancer Research.

Allen DH, Lepple-Wienhues A, Cahalan MD. Ion Channel Phenotype of Melanoma Cell Lines, The Journal of Membrane Biology, 1997, pp. 27-34, vol. 155, No. 1, Springer.

Nilius B, Wohlrab W. Potassium Channels and Regulation of Proliferation of Human Melanoma Cells, The Journal of Physiology, 1992, pp. 537-548, vol. 445, Cambridge University Press.

Nilius B, Bohm T, Wohlrab W. Properties of a Potassium-Selective Ion Channel in Human Melanoma Cells, Pflagers Archive European Journal of Physiology, Nov. 1990, pp. 269-277, vol. 417, No. 3, Springer International.

Cartman ML, Morris JA, Huddart H, Staff WG. Electrolyte Homeostasis in Urothelial Neoplasia: The Effects of Amiloride, British Journal of Urology, May 1995, pp. 599-603. vol. 75, No. 5, Blackwell Science, Ltd.

Chien JL, Warren Jr. Free Calcium and Calmodulin Levels in Acinar Carcinoma and Normal Acinar Cells of Rat Pancreas, International Journal of Pancreatology, Mar. 1988, pp. 113-127, vol. 3, No. 2-3, Elsevier.

Kim JA, Kang YS, Jung Mw, Lee SH, Lee YS. Involvement of Ca2+ Influx in the Mechanism of Tamoxifen-Induced Apoptosis in HepG2 Human Hepatoblastoma Cells, Cancer Letters, Dec. 1999, pp. 115-123, vol. 147, No. 1-2, Elsevier.

Gutierrez AA, Arias JM, Garcia L, Mas-Oliva J, Guerrero-Hernandez A. Activation of a Ca2+-Permeable Cation Channel by Two Different Inducers of Apoptosis in a Human Prostatic Cancer Cell Line, The Journal of Physiology, May 1999, pp. 95-107, vol. 517, Pt 1, The Physiological Society.

Tapia-Vieyra JV, Mas-Oliva J. Apoptosis and Cell Death Channels in Prostate Cancer, Archives of Medical Research, 2001, pp. 175-185, vol. 32, No. 3, Elsevier Science, Inc.

Ouadid-Ahidouch H, Roudbaraki M, Delcourt P, et.al. Am. J Physiol. Cell Physiol. Jul. 2004;287(1):C125-34.

Davies, R.J., Quinn, D.A., Davisson T.H. Breast Cancer Res. and Treat.vol. 88, (Suppl. 1) S221: 6005, 2004.

Davies, R.J., Quinn, D.A., Davisson T.H. Breast Cancer Res. and Treat.vol. 88, (Suppl. 1) S222-3: 6009, 2004.

Webster, M.A., Cardiff, R.D., and Muller, W.J. Proc. Natl. Acad. Sci. U.S.A. 1995 92:7849-7853.

Jhappan, C., Geiser, A.G., Kordon, E.C., Bagheri, D., Hennighausen, L., Roberts, A.B., Smith, G.H., and Merlino, G. EMBO J. 1993 12:1835-1845. [6] Stojadinovic A, Nissan A, Gallimidi Z, et.al. J Clin Oncol Apr. 20, 2005; 23 (12):2703-15.

Stojadinovic A, Nissan A, Gallimidi Z, et.al. J Clin Oncol Apr. 20, 2005; 23(12):2703-15.

Aygiin et al: "Nipple and areola diameter in Turkish pubertal girls.",Journal of adolescent health, vol. 23, No. 1, Jul. 1, 1998, pp. 55-57, XP055115091, ISSN: 1 054-139X.

D. Scott Lind et al., "Breast Procedures," Medscape, Apr. 18, 2005, XP055093787, Retrieved from the Internet: URL: www.medscape.com/viewarticle/503006_print, retrieved on Dec. 17, 2013, the whole document.

Elble RC, Pauli Bu. Tumor Suppression by a Proapoptotic Calcium-Activated Chloride Channel in Mammary Epithelium, The Journal of Biological Chemistry, Nov. 2001, pp. 40510-40517, vol. 276, No. 44, The American Society for Biochemistry and Molecular Biology.

Kim JA, Kang YS, Lee YS. Involvement of K(+)-Cl(−)-cotransport in the Apoptosis Induced by N-Ethylmaleimide in HepG2 Human Hepatoblastoma Cells, European Journal of Pharmacology, Apr. 2001, pp. 1-5, vol. 418, Nos. 1-2, Elsevier.

Loewenstein WR. Junctional Intercellular Communication and the Control of Growth, Biochimica et Biophysica Acta , Feb. 1979, pp. 1-65, vol. 560, No. 1, Elsevier/North-Holland.

Loewenstein WR. Junctional Cell-To-Cell Communication and Growth Control, Annals of the New York Academy of Sciences, 1980, pp. 39-45, vol. 339, The New York Academy of Sciences, New York, USA.

Pauli Bu, Weinstein RS. Structure of Gap Junctions in Cultures of Normal and Neoplastic Bladder Epithelial Cells, Experientia, 1981, pp. 248-250, vol. 37, No. 3, Birkhaüser Verlag.

Slaughter DP, Southwick HW, Smejkal W. "Field Cancerization" in Oral Squamous Epithelium: Clinical Implications of Multicentric Origin, Cancer, A Journal of American Cancer, Jul. 1953, pp. 963-968, vol. 6, No. 4, J.B. Lippincott Company, Philadelphia, PA, USA.

Bernstein JM, Gorfien J, Noble B, Yankaskas JR. Nasal polyposis: Immunohistochemistry and Bioelectrical Findings (A Hypothesis for the Development of Nasal Polyps), The Journal of Allergy and Clinical Immunology, Feb. 1997, pp. 165-175, vol. 99, No. 2, Mosby.

Bernstein JM, Yankaskas JR. Increased Ion transport in Cultured Nasal Polyp Epithelial Cells, Archives of Otolaryngology of Head & Neck Surgery, Sep. 1994, pp. 993-996, vol. 120, No. 9, American Medical Association.

Marina AA, Iliev IG, Schwalke MA, Gonzalez E, Marler KC, Flanagan CA. Association Between Cell Membrane Potential and Breast Cancer, Tumour Biology, 1994, pp. 82-89, vol. 15, No. 2.

Morimoto T, Kinouchi Y, Iritani T, Kimura S, Konishi Y, Mitsuyama N et al. Measurement of the Electrical Bio-Impedance of Breast Tumors, European Surgical Research, Apr. 1990, pp. 86-92, vol. 22, No. 2, S. Karger Medical and Scientific Publishers.

Thurnherr N, Deschner EE, Stonehill EH, Lipkin M. Induction of Adenocarcinomas of the Colon in Mice by Weekly Injections of 1,2-dimethylhydrazine, Cancer Research, May 1973, pp. 940-945, vol. 33, No. 5.

Hebestreit A, Kersting U, Basler B, Jeschke R, Hebestreit H. Exercise Inhibits Epithelial Sodium Channels in Patients With Cystic Fibrosis, American Journal of Respiratory and Critical Care Medicine, Jul. 2001, pp. 443-446, vol. 164, No. 3.

Orlando RC, Powell DW, Croom RD, Berschneider HM, Boucher RC, Knowles MR. Colonic and Esophageal Transepithelial Potential Difference in Cystic Fibrosis, Gastroenterology, Apr. 1989, pp. 1041-1048, vol. 96, No. 4, American Gastroentrological Association.

(56) References Cited

OTHER PUBLICATIONS

Hay JG, Geddes DM. Transepithelial Potential Difference in Cystic Fibrosis, The Journal of the British Thoracic Society, Jul. 1985, pp. 493-496, vol. 40, No. 7, British Medical Association, London, England.

Knowles M, Gatzy J, Boucher R. Increased Bioelectric Potential Difference Across Respiratory Epithelia in Cystic Fibrosis, New England Journal of Medicine, Dec. 1981, pp. 1489-1495, vol. 305, No. 25, Massachusets Medical Society.

Oksiejczuk E, Figaszewski Z. Electrokinetic Potential of Lung Cancer Cells, Rocziniki Akademii Medycznej Bialymstoku, 1997, pp. 340-354, vol. 42, Supplement 1.

Marina AA, Morris DM, Schwalke MA, Iliev IG, Rogers S. Electrical Potential Measurements in Human Breast Cancer and Benign Lesions, Tumour Biology, Jan. 1994, pp. 147-152, vol. 15, No. 3, S. Karger.

Broggi G, Franzini A. Value of Serial Stereotactic Biopsies and Impedance Monitoring in the Treatment of Deep Brain Tumours, Journal of Neurology Neurosurgery and Psychiatry, May 1981, pp. 397-401, vol. 44, No. 5, British Medical Association, London, England.

Fukuda M, Shimizu K, Okamoto N, Arimura T, Ohta T, Yamaguchi S et al. Prospective Evaluation of Skin Surface Electropotentials in Japanese Patients With Suspicious Breast Lesions, Japanese Journal of Cancer Research, Oct. 1996, pp. 1092-1096, vol. 87, No. 10, Elsevier Science, Ltd., Ireland and Business Center for Academic Societies, Japan.

Chauveau N, Hamzaoui L, Rochaix P, Rigaud B, Voigt JJ, Morucci JP. Ex Vivo Discrimination Between Normal and Pathological Tissues in Human Breast Surgical Biopsies Using Bioimpedance Spectroscopy, Annals of the New York Academy of Sciences, 1999, pp. 42-50, vol. 873, The New York Academy of Science, New York, NY, USA.

dA Silva Je, De SA JP, Jossinet J. Classification of Breast Tissue by Electrical Impedance Spectroscopy, Medical and Biological Engineering & Computing, Jan. 2000, pp. 26-30, vol. 38, No. 1.

Jossinet J. Variability of Impedivity in Normal and Pathological Breast Tissue, Medical & Biological Engineering & Computing, Sep. 1996, pp. 246-350, vol. 34, No. 5.

Jossinet J. The Impedivity of Freshly Excised Human Breast Tissue, Physiological Measurement, Feb. 1998, pp. 61-75, vol. 19, No. 1, Institute of Physics Publishing.

Jossinet J, Schmitt M. A Review of Parameters for the Bioelectrical Characterization of Breast Tissue, Annals of the New York Academy of Sciences, 1999, pp. 30-41, vol. 873, The New York Academy of Sciences, New York, NY.

Brown BH, Tidy JA, Boston K, Blackett AD, Smallwood RH, Sharp F. Relation Between Tissue Structure and Imposed Electrical Current Flow in Cervical Neoplasia, The Lancet, Mar. 2000, pp. 892-895, vol. 355, No. 9207, The Lancet Publishing Group, Ltd., Elsevier Sciences Ltd.

Cherepenin V, Karpov A, Korjenevsky A, Kornienko V, Mazaletskaya A, Mazourov D et al. A 3D Electrical Impedance Tomography (EIT) System for Breast Cancer Detection, Physiological Measurement, Feb. 2001, pp. 9-18, vol. 22, No. 1, Institute of Physics Publishing.

Gonzalez-Correa CA, Brown BH, Smallwood RH, Kalia N, Stoddard CJ, Stephenson TJ et al. Virtual Biopsies in Barrett's Esophagus Using an Impedance Probe, Annals of New York Academy of Sciences, 1999, pp. 313-321, vol. 873, The New York Academy of Sciences, New York, NY, USA.

Gorecki J, Dolan EJ, Tasker RR, Kucharczyk W. Correlation of CT and MR With Impedance Monitoring and Histopathology in Stereotactic Biopsies, The Canadian Journal of Neurological Sciences, May 1990, pp. 184-189, vol. 17, No. 2.

Kimura S, Morimoto T, Uyama T, Monden Y, Kinouchi Y, Iritani T. Application of Electrical Impedance Analysis for Diagnosis of a Pulmonary Mass, Chest, 1994, pp. 1679-1682, vol. 105, No. 6, Official Publication of American College of Chest Physicians.

Malich A, Fritsch T, Anderson R, Boehm T, Freesmeyer MG, Fleck M et al. Electrical Impedance Scanning for Classifying Suspicious Breast Lesions: First Results, European Radiology, 2000, pp. 1555-1561, vol. 10, No. 10, Springer-Verlag.

Malich A, Boehm T, Facius M, Freesmeyer MG, Fleck M, Anderson R Et al. Differentiation of Mammographically Suspicious Lesions: Evaluation of Breast Ultrasound, MRI Mammography and Electrical Impedance Scanning as Adjunctive Technologies in Breast Cancer Detection, Clinical Radiology, Apr. 2001, pp. 278-283, vol. 56, No. 4, WB Saunders Company Ltd.

Malich A, Fritsch T, Mauch C, Boehm T, Freesmeyer M, Fleck M et al. Electrical impedance Scanning: A New Technique in the Diagnosis of Lymph Nodes in Which Malignancy is Suspected on Ultrasound, British Journal of Radiology, 2001, pp. 42-47, vol. 74, No. 877.

Morimoto T, Kimura S, Konishi Y, Komaki K, Uyama T, Monden Y et al. A Study of the Electrical Bio-Impedance of Tumors, Journal of Investigative Surgeries, 1993, pp. 25-32, vol. 6, No. 1, Taylor & Francis, New York, USA.

Ohmine Y, Morimoto T, Kinouchi Y, Iritani T, Takeuchi M, Monden Y. Noninvasive Measurement of the Electrical Bioimpedance of Breast Tumors, Anticancer Research, Jun. 2000, pp. 1941-1946, vol. 20, No. 3B.

Piperno G, Frei EH, Moshitzky M. Breast Cancer Screening by Impedance Measurements, Frontiers in Medical and Biological Engineering, 1990, pp. 111-117, vol. 2, No. 2.

Poupa V, Setka J, Vrana J. [Diagnosis of Malignant Diseases of the Mucosa of the Gastrointestinal Tract by Impedance Measurement Using the DIACA Apparatus], Rozhledy Chirurgii, 1986, pp. 316-321, vol. 65, No. 5.

Setka J, Vrana J. [Impedance of the Recto-Sigmoidal Mucosa Measured by Endoscopy in the Diagnosis of Rectal Neoplasms], Archives Francaises des Maladies de L'Appareil Digestif, 1969, pp. 477-482, vol. 58, No. 7, Masson & Cie, Paris, France.

Setka J, Vrana J. [Impedance in the Endoscopy of Rectal Neoplasms], Sb Ornik Lekarsky, 1970, pp. 89-93, vol. 72, No. 4.

Brown BH. Impedance Tomography and Spectroscopy: What can and what will we see? In: Sverre Grimnes, Ørjan G.Martinsen, Heidi Bruvoll, editors. Proceedings XI International Conference on Electrical Bio-Impedance. Oslo, Norway, University of Oslo, 2001: 9-13.

Thompson SM, Suzuki Y, Schultz SG. The Electrophysiology of Rabbit Descending Colon. I. Instantaneous Transepithelial Current-Voltage Relations and the Current-Voltage Relations of the Na-Entry Mechanism, Journal of Membrane Biology, 1982, pp. 41-45, vol. 66, No. 1, Springer-Verlag, New York New York, USA.

Brasitus TA, Dudeja PK, Foster ES. 1,2-Dimethylhydrazine-induced Alterations in Na+-H+ Exchange in Rat Colonic Brush-Border Membrane Vesicles, Biochimica et Biophysica Acta, Mar. 1988, pp. 483-488, vol. 938, No. 3, Elsevier.

Davies RJ, Asbun H, Thompson SM, Goller DA, Sandle GI. Uncoupling of Sodium Chloride Transport in Premalignant Mouse Colon, Gastroenterology, Jun. 1990, pp. 1502-1508, vol. 98, No. 6, American Gastroenterological Association.

Fraser GM, Portnoy M, Bleich M, Ecke D, Niv Y, Greger R et al. Characterization of Sodium and Chloride Conductances in Preneoplastic and Neoplastic Murine Colonocytes, Pflugers Archive European Journal of Physiology, Nov. 1997, pp. 801-808, vol. 434, No. 6, Springer.

Schwan, H.P., Electrical Properties of Tissue and Cell Suspensions in: "Advances in Biological and Medical Physics," J.H. Lawrence and C.A. Tobias, Eds. vol. V, 1957, p. 147, Aladdin Press, Inc., New York.

Gonzalez-Correa CA, Brown BH, Smallwood RH, Kalia N, Stoddard CJ, Stephenson TJ et al. Assessing the Conditions for In Vivo Electrical Virtual Biopsies in Barrett's Oesophagus, Medical & Biological Engineering & Computing, Jul. 2000, pp. 373-376, vol. 38, No. 4.

Farinha, BS, et al., Skin Impedance Reduction for Electrophysiology Measurements Using Ultrasonic Skin Permeation, Biomedical Instrumentation & Technology, Jan./Feb. 2006, pp. 72-77.

Hope et al., Technology review: The use of electrical impedance scanning in the detection of breast cancer, Breast Cancer Res 2004, 6:69-74.

Partial European Search Report, EP 03731268, dated Feb. 24, 2009.

Thielecke Hagen et al: Biohybrid microarrays: Impedimetric biosensors with 3D in vitro tissues for toxicological and biomedical screening Fresenius Journal of Analytical Chemistry, vol. 369, No. 1, Jan. 2001, pp. 23-29, XP002516085 ISSN: 0937-0633.

* cited by examiner

METHOD AND SYSTEM FOR DETECTING ELECTROPHYSIOLOGICAL CHANGES IN PRE-CANCEROUS AND CANCEROUS BREAST TISSUE AND EPITHELIUM

CROSS-REFERENCE TO RELATED APPLICATIONS

This application is a continuation of U.S. patent application Ser. No. 12/589,434, filed on Oct. 23, 2009, which is a divisional of U.S. application Ser. No. 10/717,074, filed on Nov. 19, 2003, now U.S. Pat. No. 7,630,759, granted Dec. 8, 2009, which is a continuation-in-part of U.S. application Ser. No. 10/151,233, filed on May 20, 2002, now U.S. Pat. No. 6,922,586, granted Jul. 26, 2005. The disclosures of the above-mentioned application and granted patents are hereby incorporated by reference herein. Applicant also incorporates herein by reference the disclosure of U.S. application Ser. No. 10/716,789, filed on Nov. 19, 2003, entitled "Electrophysiological Approaches to Assess Resection and Tumor Ablation Margins and Responses to Drug Therapy", Richard J. Davies, inventor.

BACKGROUND OF THE INVENTION

The present invention relates generally to the detection of abnormal or cancerous tissue, and more particularly, to the detection of changes in the electrophysiological characteristics of abnormal or cancerous tissue and to changes in those electrophysiological characteristics related to the functional, structural and topographic (the interaction of shape, position and function) relationships of the tissue during the development of malignancy. These measurements are made in the absence and presence of pharmacological and hormonal agents to reveal and accentuate the electrophysiological characteristics of abnormal or cancerous tissue.

Cancer is a leading cause of death in both men and women in the United States. Difficulty in detecting abnormal pre-cancerous or cancerous tissue before treatment options become non-viable is one of the reasons for the high mortality rate. Detecting of the presence of abnormal or cancerous tissues is difficult, in part, because such tissues are largely located deep within the body, thus requiring expensive, complex, invasive, and/or uncomfortable procedures. For this reason, the use of detection procedures is often restricted until a patient is experiencing symptoms related to the abnormal tissue. Many forms of cancers or tumors, however, require extended periods of time to attain a detectable size (and thus to produce significant symptoms or signs in the patient). It is often too late for effective treatment by the time the detection is performed with currently available diagnostic modalities.

Breast cancer is the most common malignancy affecting women in the Western World. The reduction in mortality for this common disease depends on early detection. The mainstay of early detection are X-ray mammography and clinical breast examination. Both are fraught with problems of inaccuracy. For example, mammography has a lower sensitivity in women with dense breasts, and is unable to discriminate between morphologically similar benign or malignant breast lesions.

Clinical breast examinations are limited because lesions less than one cm are usually undetectable and larger lesions may be obscured by diffuse nodularity, fibrocystic change, or may be too deep in the breast to enable clinical detection. Patients with positive mammogaphic or equivocal clinical findings often require biopsy to make a definitive diagnosis. Moreover, biopsies may be negative for malignancy in up to 80% of patients.

Accordingly, mammography and clinical breast examination have relatively poor specificity in diagnosing breast cancer. Therefore many positive mammographic findings or lesions detected on clinical breast examination ultimately prove to be false positives resulting in physical and emotional trauma for patients. Improved methods and technologies to identify patients who need to undergo biopsy would reduce healthcare costs and avoid unnecessary diagnostic biopsies.

Other technologies have been introduced in an attempt to improve on the diagnostic accuracy attainable with mammography and clinical breast examination alone. Breast ultrasound is helpful in distinguishing between cystic or solid breast lesions and may be useful in guiding needle or open biopsies. However, such techniques are unable to determine whether a solid mass, or calcifications are benign or malignant. Magnetic resonance imaging has been introduced in an attempt to improve on the accuracy of mammography. Its high cost and low specificity limit its general applicability for diagnosing and screening for breast cancer. Nuclear imaging with Positron Emission Tomogaphy (PET) has a lower sensitivity for small lesions, but is limited by cost.

One proposed method for early detection of cancerous and pre-cancerous tissue includes measuring of the electrical impedance of biological tissue. For example, U.S. Pat. No. 3,949,736 discloses a low-level electric current passed through tissue, with a measurement of the voltage drop across the tissue providing an indirect indication of the overall tissue impedance. This method teaches that a change in impedance of the tissue is associated with an abnormal condition of the cells composing the tissue, indicating a tumor, carcinoma, or other abnormal biological condition. This disclosure, however, does not discuss either an increase or decrease in impedance associated with abnormal cells, nor does it specifically address tumor cells.

The disadvantage of this and similar systems is that the DC electrical properties of the epithelium are not considered. Most common malignancies develop in an epithelium (the cell layer that lines a hollow organ, such as the bowel, or ductal structures such as the breast or prostate), that maintains a transepithelial electropotential. Early in the malignant process the epithelium loses its transepithelial potential, particularly when compared to epithelium some distance away from the developing malignancy. The combination of transepithelial electropotential measurements with impedance are more accurate in diagnosing pre-cancerous and cancerous conditions.

Another disadvantage of the above referenced system is that the frequency range is not defined. Certain information is obtained about cells according to the range of frequencies selected. Different frequency bands may be associated with different structural or functional aspects of the tissue. See, for example, F. A. Duck, *Physical Properties of Tissues*, London: Academic Press, 2001; K. R. Foster, H. P. Schwan, *Dielectric properties of tissues and biological materials: a critical review*, Crit. Rev. Biomed. Eng., 1989, 17(1): 25-104. For example at high frequencies (>1 GHz) molecular structure has a dominating effect on the relaxation characteristics of the impedance profile. Relaxation characteristics include the delay in the response of a tissue to a change in the applied electric field. For example, an applied AC current results in voltage change across the tissue which will be delayed or phase shifted, because of the impedance characteristics of the tissue. Relaxation and dispersion characteristics of the tissue vary according to the frequency of the applied signal.

At lower frequencies, such as <100 Hz, or the so called α-dispersion range, alterations in ion transport and charge accumulations at large cell membrane interfaces dominate the relaxation characteristics of the impedance profile. In the frequency range between a few kHz and 1 MHz, or the so-called β-dispersion range, cell structure dominates the relaxation characteristics of the epithelial impedance profile. Within this range at low kHz frequencies, most of the applied current passes between the cells through the paracellular pathway and tight junctions. At higher frequencies in the β-dispersion range the current can penetrate the cell membrane and therefore passes both between and through the cells, and the current density will depend on the composition and volume of the cytoplasm and cell nucleus. Characteristic alterations occur in the ion transport of an epithelium during the process of malignant transformation affecting the impedance characteristics of the epithelium measured at frequencies in the α-dispersion range. Later in the malignant process, structural alterations with opening of the tight junctions and decreasing resistance of the paracellular pathways, together with changes in the composition and volume of the cell cytoplasm and nucleus, affect the impedance measured in the β-dispersion range.

Another disadvantage with the above referenced system is that the topography of altered impedance is not examined. By spacing the measuring electrodes differently the epithelium can be probed to different depths. The depth that is measured by two surface electrodes is approximately half the distance between the electrodes. Therefore electrodes 1 mm apart will measure the impedance of the underlying epithelium to a depth of approximately 500 microns. It is known, for example, that the thickness of bowel epithelium increases at the edge of a developing tumor to $1356\pm208\mu$ compared with $716\pm112\mu$ in normal bowel. D. Kristt, et al. *Patterns of proliferative changes in crypts bordering colonic tumors: zonal histology and cell cycle marker expression. Pathol. Oncol. Res* 1999; 5(4): 297-303. Thickening of the ductal epithelium of the breast is also observed as ductal carcinoma in-situ develops. By comparing the measured impedance between electrodes spaced approximately 2.8 mm apart and compared with the impedance of electrodes spaced approximately 1.4 mm apart, information about the deeper and thickened epithelium may be obtained. See, for example, L. Emtestam & S. Ollmar. *Electrical impedance index in human skin: measurements after occlusion, in 5 anatomical regions and in mild irritant contact dermatitis. Contact Dermatitis* 1993; 28(2): 104-108.

Another disadvantage of the above referenced methods is that they do not probe the specific conductive pathways that are altered during the malignant process. For example, potassium conductance is reduced in the surface epithelium of the colon early in the malignant process. By using electrodes spaced less than 1 mm apart with varying concentrations of potassium chloride the potassium conductance and permeability may be estimated in the surface epithelium at a depth from $<500\mu$ to the surface.

A number of non-invasive impedance imaging techniques have been developed in an attempt to diagnose breast cancer. Electrical impedance tomography (EIT) is an impedance imaging technique that employs a large number of electrodes placed on the body surface. The impedance measurements obtained at each electrode are then processed by a computer to generate a 2D or 3D reconstructed tomographic image of the impedance and its distribution in 2 or 3 dimensions. This approach relies on the differences in conductivity and impedivity between different tissue types and relies on data acquisition and image reconstruction algorithms which are difficult to apply clinically.

The majority of EIT systems employ "current-driving mode," which applies a constant AC current between two or more current-passing electrodes, and measures the voltage drop between other voltage-sensing electrodes on the body surface. Another approach is to use a "voltage-driving approach," which applies a constant AC voltage between two or more current-passing electrodes, and then measures the current at other current-sensing electrodes. Different systems vary in the electrode configuration, current or voltage excitation mode, the excitation signal pattern, and AC frequency range employed.

Another disadvantage with using EIT to diagnose breast cancer is the inhomogeneity of breast tissue. The image reconstruction assumes that current passes homogeneously through the breast tissue which is unlikely given the varying electrical properties of different types of tissue comprising the breast. In addition image reconstruction depends upon the calculation of the voltage distribution on the surface of the breast from a known impedance distribution (the so called forward problem), and then estimating the impedance distribution within the breast from the measured voltage distribution measured with surface electrodes (the inverse problem). Reconstruction algorithms are frequently based on finite element modeling using Poisson's equation and with assumptions with regard to quasistatic conditions, because of the low frequencies used in most EIT systems.

Other patents, such as U.S. Pat. Nos. 4,955,383 and 5,099,844, disclose that surface electropotential measurements may be used to diagnose cancer. Empirical measurements, however, are difficult to interpret and use in diagnosis. For example, the above referenced inventions diagnose cancer by measuring voltage differences (differentials) between one region of the breast and another and then comparing them with measurements in the opposite breast. Changes in the measured surface potential may be related to differences in the impedance characteristics of the overlying skin. This fact is ignored by the above referenced and similar inventions, resulting in a diagnostic accuracy of 72% or less. J. Cuzick et al. *Electropotential measurements as a new diagnostic modality for breast cancer. Lancet* 1998; 352(9125): 359-363; M. Faupel et al. *Electropotential evaluation as a new technique for diagnosing breast lesions. Eur. J. Radiol.* 1997; 24 (1): 33-38. Neither AC impedance, or surface DC measurement approaches, measure the transepithelial breast DC potential or AC impedance characteristics of the breast epithelium.

Other inventions that use AC measurement, such as U.S. Pat. No. 6,308,097, also have a lower accuracy than may be possible with a combination of DC potential measurements and AC impedance measurements, that also measure the transepithelial electrical properties of mammary epithelium. Electrical impedance scanning (EIS) also known as electrical impedance mapping (EIM) avoids the limitations of complex image reconstruction encountered with EIT. The above referenced system diagnoses cancer by only measuring decreased impedance (increased conductance) and changes in capacitance over a cancer. It does not measure the mammary transepithelial impedance characteristics of the breast. There are several other limitations to this approach. Inaccuracies may occur because of air bubbles. Underlying bones, costal cartilages, muscle and skin may result in high conductance regions, which produce false positives. Depth of measurement is limited to 3-3.5 cm, which will result in false negatives for lesions on the chest wall. It is also not possible to localize lesions using this approach.

Another potential source of information for the detection of abnormal tissue is the measurement of transport alterations in the epithelium. Epithelial cells line the surfaces of the body and act as a barrier to isolate the body from the outside world. Not only do epithelial cells serve to insulate the body, but they also modify the body's environment by transporting salts, nutrients, and water across the cell barrier while maintaining their own cytoplasmic environment within fairly narrow limits. One mechanism by which the epithelial layer withstands the constant battering is by continuous proliferation and replacement of the barrier. This continued cell proliferation may partly explain why more than 80% of cancers are of epithelial cell origin. Moreover, given their special abilities to vectorially transport solutes from blood to outside and vice versa, it appears that a disease process involving altered growth regulation may have associated changes in transport properties of epithelia.

It is known that the addition of serum to quiescent fibroblasts results in rapid cell membrane depolarization. Cell membrane depolarization is an early event associated with cell division. Depolarization induced by growth factors appears biphasic in some instances but cell division may be stimulated without depolarization. Cell membrane depolarization is temporally associated with $Na^+$ influx, and the influx persists after repolarization has occurred. Although the initial $Na^+$ influx may result in depolarization, the increase in sodium transport does not cease once the cell membrane has been repolarized, possibly due to Na/K ATPase pump activation. Other studies also support the notion that $Na^+$ transport is altered during cell activation. In addition to altered $Na^+$-transport, $K^+$-, and $Cl^-$-transport is altered during cell proliferation.

A number of studies have demonstrated that proliferating cells are relatively depolarized when compared to those that are quiescent or non-dividing. Differentiation is associated with the expression of specific ion channels. Additional studies indicate that cell membrane depolarization occurs because of alterations in ionic fluxes, intracellular ionic composition and transport mechanisms that are associated with cell proliferation.

Intracellular $Ca^{2+}$ ($Ca^{2+}_i$) and pH ($pH_i$) are increased by mitogen activation. Cell proliferation may be initiated following the activation of phosphatidylinositol which releases two second messengers, 1,2-diacylglycerol and inosotol-1,4,5-triphosphate, which triggers $Ca^{2+}_i$ release from internal stores. $Ca^{2+}_i$ and $pH_i$ may then alter the gating of various ion channels in the cell membrane, which are responsible for maintaining the voltage of the cell membrane. Therefore, there is the potential for interaction between other intracellular messengers, ion transport mechanisms, and cell membrane potential. Most studies have been performed in transformed and cultured cells and not in intact epithelia during the development of cancer.

It was known for some time that cancer cells are relatively depolarized compared with non-transformed cells. It has been suggested that sustained cell membrane depolarization results in continuous cellular proliferation, and that malignant transformation results as a consequence of sustained depolarization and a failure of the cell to repolarize after cell division. C. D. Cone Jr., *Unified theory on the basic mechanism of normal mitotic control and oncogenesis. J. Theor. Biol.* 1971; 30(1): 151-181; C. D. Cone Jr., C. M. Cone. *Induction of mitosis in mature neurons in central nervous system by sustained depolarization. Science* 1976; 192(4235): 155-158; C. D. Cone, Jr. *The role of the surface electrical transmembrane potential in normal and malignant mitogenesis. Ann. N.Y. Acad. Sci.* 1974; 238: 420-435. A number of studies have demonstrated that cell membrane depolarization occurs during transformation and carcinogenesis. Other studies have demonstrated that a single ras-mutation may result in altered ion transport and cell membrane depolarization. Y. Huang, S. G. Rane, *Single channel study of a Ca(2+)-activated K+ current associated with ras induced cell transformation. J. Physiol.* 1993; 461: 601-618. For example, there is a progressive depolarization of the colonocyte cell membrane during 1,2 dimethylhydrazine (DMH)-induced colon cancer in $CF_1$ mice. The $V_A$ (apical membrane voltage) measured with intracellular microelectrodes in histologically "normal" colonic epithelium depolarized from −74.9 mV to −61.4 mV after 6 weeks of DMH treatment and to −34 mV by 20 weeks of treatment. The cell membrane potential in a benign human breast epithelial cell line (MCF-10A) was observed to be −50±4 mV (mean±SEM) and was significantly depolarized at −35±1 mV (p<0.002) in the same cell line after ras-transformation (the MCF-10AT cell line).

While epithelial cells normally maintain their intracellular sodium concentration within a narrow range, electronmicroprobe analysis suggests that cancer cells exhibit cytoplasmic sodium/potassium ratios that are three to five times greater than those found in their non-transformed counterparts. These observations partly explain the electrical depolarization observed in malignant or pre-malignant tissues, because of the loss of $K^+$ or $Na^+$ gradients across the cell membrane.

In addition to cell membrane depolarization, and altered intracellular ionic activity, other studies have shown that there may be a decrease in electrogenic sodium transport and activation of non-electrogenic transporters during the development of epithelial malignancies. These changes may affect or occur as a consequence of altered intracellular ionic composition.

In addition to cell membrane depolarization, and altered intracellular ionic activity, other studies have shown that there may be a decrease in electrogenic sodium transport and activation of non-electrogenic transporters during the development of epithelial malignancies. These changes may occur as a consequence of altered intracellular ionic composition. Other specific ion transport alterations have been described in colon, prostate, breast, uterine cervix, melanoma, urothelium, and pancreas during proliferation, differentiation, apoptosis, and carcinogenesis.

Apoptosis or physiological cell death is down-regulated during the development of malignancy. Ion transport mechanisms affected by apoptosis include the influx of $Ca^{2+}$, non-selective $Ca^{2+}$-permeable cation channels, calcium-activated chloride channels, and $K^+$-$Cl^-$-cotransport. J. A. Kim et al. *Involvement of Ca2+ influx in the mechanism of tamoxifen-induced apoptosis in Hep2G human hepatoblastoma cells. Cancer Lett.* 1999; 147(1-2): 115-123; A. A. Gutierrez et al. *Activation of a Ca2+-permeable cation channel by two different inducers of apoptosis in a human prostatic cancer cell line. J. Physiol.* 1999; 517 (Pt. 1): 95-107; J. V. Tapia-Vieyra, J. Mas-Oliva. *Apoptosis and cell death channels in prostate cancer. Arch. Med. Res.* 2001; 32(3): 175-185; R. C. Elble, B. U. Pauli. *Tumor Suppression by a Proapoptotic Calcium-Activated Chloride Channel in Mammary Epithelium. J. Biol. Chem.* 2001; 276(44): 40510-40517.

Loss of cell-to-cell communication occurs during carcinogenesis. This results in defective electrical coupling between cells, which is mediated via ions and small molecules through gap junctions, which in turn influences the electrical properties of epithelia.

Epithelial cells are bound together by tight junctions, which consist of cell-to-cell adhesion molecules. These adhesion proteins regulate the paracellular transport of molecules and ions between cells and are dynamic structures that can tighten the epithelium, preventing the movement of substances, or loosen allowing substances to pass between cells. Tight junctions consist of integral membrane proteins, claudins, occludins and JAMs (junctional adhesion molecules). Tight junctions will open and close in response to intra and extracellular stimuli.

A number of substances will open or close tight junctions. The proinflammatory agent TGF-alpha, cytokines, IGF and VEGF opens tight junctions. Zonula occludens toxin, nitric oxide donors, and phorbol esters also reversibly open tight junctions. Other substances close tight junctions including calcium, H2 antagonists and retinoids. Various hormones such as prolactin and glucocorticoids will also regulate the tight junctions. Other substances added as drug formulations act as non-specific tight junction modulators including chitosan and wheat germ agglutinin.

The above referenced substances and others may act directly or indirectly on the tight junction proteins, which are altered during carcinogenesis. For example claudin-7 is lost in breast ductal epithelium during the development of breast cancer. The response of the tight junctions varies according to the malignant state of the epithelium and their constituent proteins. As a result the opening or closing of tight junctions is affected by the malignant state of the epithelium.

Polyps or overtly malignant lesions may develop in a background of disordered proliferation and altered transepithelial ion transport. Experimental animal studies of large bowel cancer have demonstrated that transepithelial depolarization is an early feature of the pre-malignant state. In nasal polyp studies, the lesions had a higher transepithelial potential, but these lesions were not pre-malignant in the same sense as an adenomatous or pre-malignant colonic polyp, that are usually depolarized. Electrical depolarization has been found in biopsies of malignant breast tissue. Recently alterations in impedance have been found to be associated with the pre-malignant or cancerous state in breast and bowel.

It has been discovered that transepithelial depolarization was a specific event associated with colonic carcinogenesis in $CF_1$ mice. The more susceptible site, the distal colon, underwent about a 30% decrease in transepithelial potential ($V_T$) after only four weeks of carcinogen treatment. This was before histological changes developed. A non-specific cytotoxic agent (5-fluorouracil), administered over the same period did not cause a reduction in $V_T$ in the same model. The reduction in $V_T$ was confirmed in a subsequent study where almost a 60% reduction was observed after carcinogen treatment. It has also been discovered that, although $V_T$ is invariably higher when measured in vivo, the "premalignant" colonic epithelium is usually depolarized when compared to normal colon.

DC electrical potential alterations have been used to diagnose non-malignant conditions such as cystic fibrosis, cancer in animal models, human cells or tissue and in man. Differences in impedance between normal tissue and cancer have been described in animal models in vitro human tissue in vitro and have been applied to in vivo cancer diagnosis.

DC potential measurements have not been combined with impedance measurements to diagnose cancer because the electrophysiological alterations that accompany the development of cancer have not been well understood or fully characterized. Surface measurements of potential or impedance are not the same as measurements performed across the breast epithelium, and described below, where electrical contact is made between the luminal surface of the duct and the overlying skin. Transepithelial depolarization is an early event during carcinogenesis, which may affect a significant region of the epithelium (a "field defect"). This depolarization is accompanied by functional changes in the epithelium including ion transport and impedance alterations. Early on in the process these take the form of increased impedance because of decreased specific electrogenic ion transport processes. As the tumor begins to develop in the pre-malignant epithelium, structural changes occur in the transformed cells such as a break down in tight junctions and nuclear atypia. The structural changes result in a marked reduction in the impedance of the tumor. The pattern and gradient of electrical changes in the epithelium permit the diagnosis of cancer from a combination of DC electrical and impedance measurements.

Another reason that DC electropotential and impedance measurements have not been successfully applied to cancer diagnosis is that transepithelial potential and impedance may be quite variable and are affected by the hydration state, dietary salt intake, diurnal or cyclical variation in hormonal level or non-specific inflammatory changes and other factors. In the absence of knowledge about the physiological variables which influence transepithelial potential and impedance these kind of measurement may not be completely reliable to diagnose pre-malignancy or cancer.

Furthermore, a detailed understanding of the functional and morphological alterations that occur during carcinogenesis permits appropriate electrical probing for a specifically identified ion transport change that is altered during cancer development. For example knowledge that electrogenic sodium absorption is altered during cancer development in breast epithelium permits the use of sodium channel blockers (amiloride) or varying sodium concentration in the ECM (electroconductive medium) to examine whether there is an inhibitable component of sodium conductance. By varying the depth of the measurement (by measuring the voltage drop across differently space electrodes), it is possible to obtain topographic and depth information about the cancerous changes in the epithelium. Using a combination of low and high frequency sine waves probing at different depths we are able to correlate the functional and morphological (structural) changes at different depths, with the impedance profile of the tissue.

The diagnostic accuracy of current technology using DC electropotentials or impedance alone have significant limitations. Sensitivity and specificity for DC electrical measurements in the breast have been reported as 90% and 55% respectively and 93% and 65% for impedance measurements. This would result in an overall diagnostic accuracy of between 72-79%, which is probably too low to result in widespread adoption. The measurement of ductal transepithelial DC potential, ductal transepithelial AC impedance spectroscopy alone, or the combination of DC electrical potentials and impedance spectroscopy will result in a diagnostic accuracy of greater than 90%, which will lead to improved clinical utility.

Breast cancer is thought to originate from epithelial cells in the terminal ductal lobular units (TDLUs) of mammary tissue. These cells proliferate and have a functional role in the absorption and secretion of various substances when quiescent and may produce milk when lactating. Functional alterations in breast epithelium have largely been ignored as a possible approach to breast cancer diagnosis. Breast epithelium is responsible for milk formation during lactation. Every month pre-menopausal breast epithelium undergoes a "rehearsal" for pregnancy with involution following menstruation. The flattened epithelium becomes more columnar as the epithelium enters the luteal phase from the follicular phase. In addition duct branching and the number of acini reach a maximum during the latter half of the luteal phase. Just before menstruation apoptosis of the epithelium occurs and the process starts over again unless the woman becomes pregnant.

Early pregnancy and lactation may be protective against breast cancer because they result in a more differentiated breast epithelium which is less susceptible to carcinogenic influences whether estrogen or other environmental factors. It therefore seems that differentiated breast epithelium is less likely to undergo malignant change. Differentiated epithelium has a distinct apical and basolateral membrane domain to enable it to maintain vectorial transport function (the production of milk). In addition, differentiated cells maintain a higher cell membrane potential to transport various ions, lactulose and other substances in and out of the duct lumen. In contrast, more proliferative epithelial cells have depolarized cell membranes and are less able to maintain vectorial ion transport. Recently the epithelial $Na^+$ channel (ENaC) and the cystic fibrosis transmembrane conductance regulator (CFTR) have been identified in mammary epithelium and both localized on the apical, or luminal side, of the epithelium. These two transporters can be probed for by using amiloride, a blocker of the ENaC, or by opening up $Cl^-$ channels regulated by CFTR using cAMP.

For example, 20 μM luminal amiloride depolarized the transepithelial potential from −5.9±0.5 mV (mean±SEM) by +3.1±0.5 mV. Forskolin (10 μM), which raises cAMP and opens $Cl^-$ channels via the CFTR hyperpolarized the breast epithelium by −2.2±0.1 mV. These changes were accompanied by an increase (17%) and subsequent decrease (19%) in transepithelial resistance respectively. In transformed breast epithelium the ENaC is down-regulated, whereas $Cl^-$ secretion may increase, similar to observations reported for carcinoma of the cervix. Non-lactating breast epithelium has relatively leaky tight junctions. This results in a paracellular shunt current, which hyperpolarizes the apical membrane of the epithelial cell. The larger the shunt current the more hyperpolarized the apical membrane and therefore the epithelium depolarizes since $TEP=V_{BL}-V_A$ and $i=TEP/R_S$. TEP=Transepithelial potential; $V_{BL}$=voltage of the basolateral membrane; $V_A$=voltage of the apical membrane; i=shunt current; $R_S$=paracellular (shunt) resistance.

Evidence that breast carcinogenesis may be associated with functional incompetence of breast epithelium also comes from a number of other sources. Some transgenic strains of mice have defective lactation. The transgenic src mouse which develops hyperplastic alveolar nodules, otherwise develops a normal mammary tree but has defective lactation. The notch4 and TGFβ transgenic mouse also demonstrate defective lactation. Cyclin D1 females have persistent lactation 6-9 months after weaning, and TGFα mice, which have a defect in apoptosis and fail to undergo epithelial regression develop hypersecretion. These data suggest that there is a relationship between epithelial function and genetic expression which affects proliferation and tumor development.

Breast cysts occur in 7% of the female population and are thought to develop in the TDLUs. Apocrine cysts have a higher potassium content than simple cysts. Apocrine cysts may be associated with the subsequent development of breast cancer. There may therefore be a fundamental change in the epithelium at risk for breast cancer development with a redistribution of electrolyte content across the cell membrane resulting in altered cyst electrolyte content and cell membrane depolarization. Although it is commonly known that during lactation the breast transports lactulose, proteins, fatty acids, immunoglobulins cholesterol, hormones, ions and water across the ductal and lobular epithelium and actively secretes milk, it is less widely appreciated that in the non-pregnant and non-lactating state the breast, throughout life exhibits excretory and absorptive function. The difference between the lactating and the non-lactating breast being of degree and the chemical constitution of the nipple duct fluid. Ductal secretions have been analyzed to diagnose biological conditions of the breast.

A number of approaches have been used to obtain ductal fluid, including a suction cup to obtained pooled secretions; nipple aspiration fluid (NAF), and more recently, cannulation of one of the 6-12 ducts that open onto the nipple surface. Substances and cells within the duct fluid may therefore be accessed to identify abnormalities that may be associated with the diseased state of the breast. One disadvantage of the above referenced approaches is the difficulty in obtaining adequate NAF or lavage fluid to perform analysis. Another disadvantage has been the inability to identify or cannulate the ducts where an abnormality in the fluid or cells may be identified.

Hung (U.S. Pat. No. 6,314,315) has suggested an electrical approach to identify ductal orifices on the nipple surface. In that disclosure it is taught that DC potential or impedance measurement may facilitate the identification of openings or orifices on the surface of the nipple. However, it is not taught that the characteristics of the DC electrical signal or impedance may characterize the condition of the breast. Moreover, it is not taught that breast transepithelial DC measurements, transepithelial AC impedance spectroscopy, alone or in combination may be used to diagnose breast cancer.

Ionic gradients exist between the fluid secretions within the breast ducts and the plasma. For example, it is known that the nipple aspirate fluid has a sodium concentration $[Na^+]$ of 123.6±33.8 mEq/l (mean±standard deviation) compared with a serum $[Na^+]$ of approximately 150 mEq/l (Petrakis1). Nulliparous women have NAF $[Na^+]$ that are approximately 10 mEq/l higher than parous women, but still significantly below serum levels. Similarly potassium concentration $[K^+]$ is significantly higher at 13.5±7.7 mEq/l in parous women and 12.9±6.0 mEq/l in nulliparous women compared with serum levels of $[K^+]$ of approximately 5.0 mEq/l. Other investigators have reported lower NAF $[Na^+]$ of 53.2 mEq/l suggesting that significant ionic gradients can be established between the plasma and duct lumen in non-lactating breast. In pregnancy these gradients are even higher for sodium with a $[Na^+]$ of 8.5±0.9 mEq/l reported in milk which is almost 20 fold lower than plasma. Chloride concentration $[Cl^-]$ in milk is almost one tenth of the concentration found in plasma with values of 11.9±0.5 mM reported. Although $[Na^+]$ and $[Cl^-]$ levels in ductal secretions rise and the $[K^+]$ falls following the cessation of lactation, significant ionic gradients are maintained between the duct lumen and plasma.

Furthermore, in women undergoing ovulatory cycles during lactation distinct changes have been observed in the ion and lactulose concentrations of breast milk. The first change occurs 5-6 days before ovulation and the second 6-7 days after ovulation. During these periods $[Na^+]$ and $[Cl^-]$ increased more than two-fold and $[K^+]$ decreased approximately 1.5-fold. It is unclear whether changes in estrogen or progesterone levels before and after ovulation are affecting the ion composition of milk. However, it is known that alterations in the ionic composition of milk influences the transepithelial electrical potential as measured in mammals.

Furthermore, it is known that various hormones affect breast epithelial ion transport. For example, prolactin decreases the permeability of the tight-junctions between breast epithelial cells, stimulates mucosal to serosal $Na^+$ flux, upregulates $Na^+:K^+:2Cl^-$ cotransport and increases the $[K^+]$ and decreases the $[Na^+]$ in milk. Glucocorticoids control the formation of tight-junctions increasing transepithelial resistance and decreasing epithelial permeability. Administration of cortisol into breast ducts late in pregnancy has been shown to increase the $[K^+]$ and decrease $[Na^+]$ of ductal secretions. Progesterone inhibits tight-junction closure during pregnancy and may be responsible for the fluctuations in ductal fluid electrolytes observed during menstrual cycle in non-pregnant women, and discussed above. Estrogen has been observed to increase cell membrane and transepithelial potential and may stimulate the opening of $K^+$-channels in breast epithelial cells. The hormones mentioned above vary diurnally and during menstrual cycle. It is likely that these variations influence the functional properties of breast epithelium altering the ionic concentrations within the lumen, the transepithelial potential and impedance properties, which are dependent upon the ion transport properties of epithelial cells and the transcellular and paracellular conductance pathways.

Accordingly, these variations can be used as diagnostic indicia of changes to breast tissue, which have to date yet to be exploited. Thus, there remains a need for effective and practical methods for detecting abnormal breast tissue.

SUMMARY OF THE INVENTION

To overcome problems and inadequacies associated with prior methods, abnormal or cancerous tissue is characterized using DC and/or impedance measurements that pass the current or signal across the breast epithelium and tumor using specially constructed electrodes. For example a nipple electrode may be used to measure the voltage and/or impedance between ductal epithelium, surrounding breast tissue, skin and surface or other electrode. The nipple electrode may also be used to pass the current along the ductal system of the breast. Another type of electrode may be used to measure the voltage and/or impedance signal, and/or pass a current and measure the signal at the individual ductal orifices at the nipple surface. Another type of electrode may be used to measure the voltage and/or impedance signal, and/or pass a current and measure the signal within individual ducts using a modified ductal probe or ductoscope which may have one or more electrodes attached to it. All of these electrodes may be used individually, in combination with one another, or with a surface probe or electrodes. Additionally DC and impedance measurements will be used in combination to more adequately characterize abnormal or cancerous tissues. DC measurements provide information about the functional state of the epithelium and can detect early pre-malignant changes and an adjacent malignancy. Impedance measurements at different frequencies using differently spaced electrodes provide depth and topographic information to give both structural (high frequency range) and functional (low frequency range) information about the tissue being probed. Abnormal or cancerous tissue can be detected and characterized by detecting and measuring transport alterations in epithelial tissues, using ionic substitutions and/or pharmacological and hormonal manipulations to determine the presence of abnormal pre-cancerous or cancerous cells. A baseline level of transepithelial DC potential, impedance or other electrophysiological property that is sensitive to alterations in transport in epithelia is measured in the tissue to be evaluated. An agent may be introduced to enhance the transport or make it possible to detect the transport alteration. The transepithelial DC potential and/or impedance of the tissue (or other electrophysiological property that may reflect or make it possible to detect alterations in the transport) are then measured. Based on the agent introduced and the measured electrophysiological parameter, the condition of the tissue is determined.

A method and system are provided for determining a condition of a selected region of breast epithelial tissue. At least two current-passing electrodes are located in contact with a first surface of the selected region of the tissue. Alternatively the current passing electrodes may pass current across the tissue or epithelium as for example between the nipple ducts, ductal lumen, epithelium, breast parenchyma and surface of the breast. Alternatively, the ducts may be accessed by a central duct catheter or ductoscope. A plurality of measuring electrodes are located in contact with the first surface of the breast as well. Initially, one or more of the measuring electrodes is used to measure the DC potential referenced to another electrode, or reference point. A signal is established between the current-passing electrodes. Impedance, associated with the established signal, is measured by one or more of the measuring electrodes. Alternatively a three-electrode system may be used for measurements whereby one electrode is used for both current injection and voltage recording. An agent is introduced into the region of tissue. The condition of the tissue is determined based on the effect of the agent on measured DC transepithelial potential, impedance or other electrophysiological characteristic. The electrodes in the described methods and apparatus can be used in contact with, in proximity to, over, or inserted into the tissues being examined. It should be understood that where the method is described in an embodiment as encompassing one of these arrangements, it is contemplated that it can also be used interchangeably with the other. For example, where the method is described as having an electrode in contact with the tissue, the method can also be used with the electrode inserted into or in proximity to the tissue. Similarly, where the method is described as having an electrode in proximity to the tissue, it is contemplated that the electrode can also be in contact with or inserted into the tissue.

In order to more accurately detect transport alterations in abnormal pre-cancerous or cancerous epithelial tissue, a pharmacological agent may be introduced to manipulate the tissue. Pharmacological agents may include agonists of specific ion transport and electrical activity, antagonists of specific ion transport and electrical activity, ionic substitutions, and/or hormonal or growth factor stimulation or inhibition of electrical activity.

Depending on the location of the tissue to be investigated, a number of methods may be used to administer the pharmacological or hormonal agents. One exemplary method includes introducing the agent directly to the tissue being investigated, via ductal infusion, perfusion, direct contact or injection. Another exemplary method includes applying the agent to the skin surface, wherein the agent acts transcutaneously, or through the skin. Yet another exemplary method includes electroporation, wherein the ductal epithelium or surface is made permeable by the passage of alternating current via electrodes in contact or penetrating the organ or epithelium of interest. The agent then passive diffuses into the organ and its constituent cells. The agent may be introduced directly into the breast ductal system using the modified nipple aspirator cup and electrode, or lavaged into a specific duct using a ductal catheter or probe. Additional exemplary methods include via inhalation, oral administration, lavage, gavage, enema, parenteral injection into a vein or artery, sublingually or via the buccal mucosa, or via intraperitoneal administration. One skilled in the art will appreciate that other methods are possible and that the method chosen is determined by the tissue to be investigated.

Thus, systems and methods consistent with the present invention use transepithelial electropotential or/and impedance measurements to diagnose pre-malignancy or cancer. Further, systems and methods consistent with the present invention use a defined set of frequencies, in combination, to characterize functional and structural alterations in pre-malignancy and cancer. By using spaced electrodes the present invention may provide topographic and geometrical (depth) information about the epithelium under examination to diagnose pre-malignancy and cancer. In one embodiment, systems and methods of the present invention use electrodes with specially formulated ECMs to provide functional information about the epithelium to diagnose pre-malignancy and cancer.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention.

DETAILED DESCRIPTION

Figure 1:
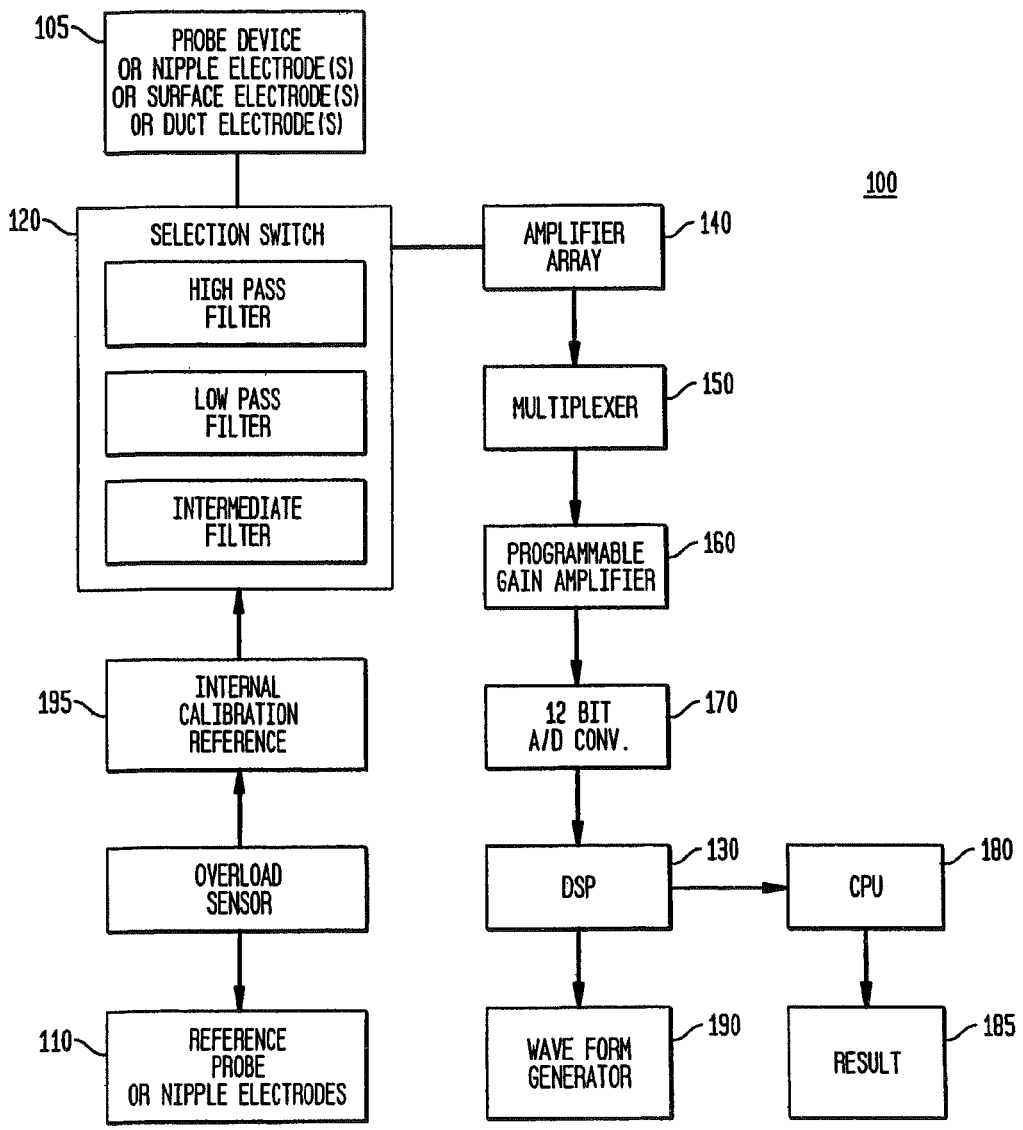
FIG. 1 is a schematic diagram of a DC and AC impedance measuring device, consistent with an embodiment of the present invention.

Reference will now be made in detail to an embodiment of the invention, an example of which is illustrated in the accompanying drawings. Wherever possible, the same reference numbers will be used throughout the drawings to refer to the same or like parts.

Overview

In order to measure the transepithelial breast DC potential it is necessary that the lumen of the duct be electrically accessed by a nipple electrode constructed to make an electrical connection between the Ag/AgCl (or similar low offset platinum/hydrogen, titanium, tin-lead alloy, nickel, aluminum, zinc, carbon, or other conductive metal or conductive polymer electrode) pellet recessed within the nipple cup. The cup is filled with an ECM (electro-conductive medium), which enters the ductal system passively, or after aspiration with a syringe or pump, making contact with the ductal lumen. A surface electrode placed at the surface of the breast completes the electrical circuit, so that measurements of transepithelial potential may be made between the ductal epithelium, or center of the tumor and the skin surface. Similar considerations have to be given to measure transepithelial AC impedance whereby the measuring electrodes measure the voltage drop and phase shift across the ductal epithelium or tumor, by utilizing a nipple electrode in combination with a skin surface electrode. Other configurations of this approach are more invasive, whereby measurement can be made between an electrode inserted via a ductoscope or nipple duct probe electrode referenced to the skin or an IV (intravenous), intradermal, or subcutaneous electrode. In another embodiment, the duct may also be accessed by a needle-electrode inserted through the skin.

In order to combine DC transepithelial measurement with impedance measurements, it is necessary to obtain baseline measurement of the DC potential using the voltage sensing electrodes, referenced to surface electrode with low-contact impedance, or the blood stream via an IV, or the interstitial body fluid via a needle electrode or electrode that permeabilizes the overlying epidermis or other epithelium, or other body reference point. The electrodes may contain different ionic concentrations, pharmacological agents or hormones in their ECMs. As used in this description, an ECM is a medium that permits transmission of electrical signals between the surface being measured and the electrode. An agent includes any ionic concentration, pharmacological agent, hormone or other compound added to the ECM or otherwise introduced to the tissue under investigation, selected to provide further information about the condition of the tissue. In another embodiment the concentrations of agents may be changed using a flow through system.

Electroconductive media can include conductive fluids, creams or gels used with external or internal electrodes to reduce the impedance (resistance to alternating current) of the contact between the electrode surface and the skin or epithelial surface. In the case DC electrodes it is also desirable that the ECM results in the lowest DC offset at the electrode surface, or an offset that can be measured. The ECM will often contain a hydrogel that will draw fluid and electrolytes from deeper layers of the skin to establish electrical contact with the surface electrode. Electrodes that are used to pass current require ECMs with high conductance. Usually this is accomplished by using ECMs with high electrolyte content.

The electrolytes frequently used are KCl (potassium chloride) because of the similar ionic mobility of these two ions in free solution, so that electrode polarization is less of a problem than when ions of different mobility are used. Other ions such as sodium may be used in ECM formulations, and the higher electrolyte concentration result in more rapid electrode equilibration.

In situations where estimations will be made of the permeability of the epithelium to specific ions, the concentration of K in the ECM will be varied so that the conductance of the epithelium to potassium may be measured electrophysiologically. An enhancer or permeant may be added to the ECM to increase the conductance of the underlying skin to the electrolyte in the ECM. Other approaches include mild surface abrasion to reduce surface skin resistance or silicon electrodes, which just penetrate the stratum corneum to reduce skin surface resistance.

In order to measure the depth of the impedance alteration, the voltage drop will be made between surface electrodes with different spacing. Spacing will be determined by knowledge of the depth to be probed. Similarly two different frequency ranges will be used to measure functional and structural changes at different depths.

In order to more accurately detect the functional transport alterations at different depths in abnormal pre-cancerous or cancerous epithelial tissue, a pharmacological agent is introduced to manipulate the tissue, while electrically probing the tissue at different frequencies and monitoring the voltage drop between differently spaced electrodes. Pharmacological agents include agonists of specific ion transport and electrical activity, antagonists of specific ion transport and electrical activity, ionic substitutions, and/or hormonal or growth factor stimulation or inhibition of electrical activity.

Depending on the location of the tissue to be investigated, a number of methods are used to administer the pharmacological or hormonal agents. One exemplary method includes introducing the agent directly to the tissue being investigated, via ductal perfusion, infusion, direct contact or injection. Another exemplary method includes applying the agent to the skin surface, wherein the agent acts transcutaneously, or through the skin. Yet another exemplary method includes electroporation, wherein the epithelium or surface is made permeable by the passage of alternating current via electrodes in contact or penetrating the surface of the breast or ductal epithelium of interest. The agent then passively diffuses into the breast and its constituent cells. Additional exemplary methods include via inhalation, oral administration, lavage, gavage, enema, parenteral injection into a vein or artery, sublingually or via the buccal mucosa, or via intraperitoneal administration. One skilled in the art will appreciate that other methods are possible and that the method chosen is determined by the tissue to be investigated.

Based on the agent introduced and the tissue being investigated, measurements of electrophysiological properties, such as impedance, are performed. Other properties that can be measured includes, transepithelial potential, changes in spontaneous oscillations in transepithelial potential or impedance associated with the malignant state, time delay in a propagation signal between electrodes, which indicates a loss of gap-junction function. If adjacent cells are electrically coupled, one can examine the loss of coupling by pharmacologically eliciting an electrical signal and measuring the signal propagation up and down-stream through surface epithelial cells. This is a functional measurement of the gap-junctions, whereas simple electrical stimulation will measure shunting of a current between the cells (a structural measurement, at least in the high frequency range).

The results of these measurements are then used to determine the condition of the investigated tissue. For example, research has indicated that specific ion transport processes are altered during the development of cancer. For example, a loss of electrogenic $Na^+$ transport, an up-regulation in Na/H exchange, a down-regulation in $K^+$ conductance, a decrease in basal $Cl^-$ absorption, and a down-regulation in c-AMP (cyclic adenosine-3',5'-cyclic monophosphate) stimulated $Cl^-$ secretion have been observed.

Thus, by administering agents appropriate to the particular epithelial tissue and measuring the associated electrophysiological characteristics, it is possible to detect abnormal pre-cancerous or cancerous tissue while the development of such tissue is at an early stage. It should be understood that the method and system of the present invention is applicable to any epithelial derived cancer, such as, but not limited to, prostate, colon, breast, esophageal, and nasopharyngeal cancers, as well as other epithelial malignancies, such as lung, gastric, uterine cervix, endometrial, skin and bladder.

Specifically, in cancers affecting mucosal or epithelial tissues, transport alterations may be sufficiently large to suggest that they are a consequence of an early mutation, affecting a large number of cells (i.e., a field defect). In this case, they may be exploited as potential biomarkers for determining which patients should be either more frequently monitored, or conversely, may be used to identify particular regions of epithelium that require biopsy. The latter is especially helpful in the case of atypical ductal hyperplasia or ductal carcinoma in situ (DCIS), which are more difficult to detect mammographically, or by clinical breast examination without having to resort to an invasive biopsy.

A number of variations are possible for devices to be used with the present invention. Further, within a device design, there are a number of aspects that may be varied. These variations, and others, are described below.

One probe or other device includes a plurality of miniaturized electrodes in recessed wells. Disposable commercially available silicon chips processing functions, such as filtering, may perform surface recording and initial electronic processing. Each ECM solution or agent may be specific to the individual electrode and reservoir on the chip. Thus, for one measurement, a particular set of electrodes is used. For another measurement, for example, at a different ionic concentration, a different set of electrodes is used. While this produces some variations, as the electrodes for one measurement are not located at the same points as for another, this system provides generally reliable results.

An alternative approach is to use fewer electrodes and use a flow-through or microfluidic system to change solutions and agents. Specifically, solutions or agents are changed by passing small amounts of electrical current to move solution or agent through channels and out through pores in the surface of the probe. In this embodiment, the electrode remains in contact with the same region of the skin or ductal epithelium, thus eliminating region-to-region variation in measurement. This approach requires time for equilibration between different solutions.

In detecting the presence of abnormal pre-cancerous or cancerous breast tissue, a hand-held probe is provided for obtaining surface measurements at the skin. The probe may include electrodes for passing current as well as for measuring. An impedance measurement may be taken between the nipple cup electrode and the hand-held probe, or may be taken between electrodes on the hand-held probe. Alternatively, a ductoscopic or non-optical ductal probe may be interfaced with one or more miniaturized electrodes. After taking initial DC measurements, a wetting/permeabilizing agent may be introduced to reduce skin impedance. The agent may be introduced using a microfluidic approach, as described above, to move fluid to the surface of the electrodes. Alternatively, surface electrodes that just penetrate the stratum corneum may be used to decrease impedance.

Regardless of the configuration of the device, FIG. 1 is a schematic of a DC and AC impedance measurement system 100 used in cancer diagnosis, consistent with the present invention. The system 100 interfaces with a probe device 105 including multiple electrodes, wherein the actual implementation of the probe device 105 depends on the organ and condition under test. The probe device 105 may incorporate the electrodes attached to a needle, body cavity, ductoscopic, non-optical ductal or surface probe. A reference probe 110 may take the form of an intravenous probe, skin surface probe, nipple-cup or ductal epithelial surface reference probe depending on the test situation and region of breast under investigation.

To avoid stray capacitances, the electrodes may be connected via shielded wires to a selection switch 120 which may select a specific probe 105 following a command from the Digital Signal Processor (DSP) 130. The selection switch 120 also selects the appropriate filter interfaced to the probe 105, such that a low pass filter is used during DC measurements and/or an intermediate or high pass filter is used during the AC impedance measurements. The selection switch 120 passes the current to an amplifier array 140 which may be comprised of multiple amplifiers or switch the signals from different electrodes through the same amplifiers when multiple electrodes are employed. In a preferred embodiment digital or analogue lock-in amplifiers are used to detect minute signals buried in noise. This enables the measurement of the signal of interest as an amplitude modulation on a reference frequency. The switching element may average, sample, or select the signal of interest depending on the context of the measurement. This processing of the signal will be controlled by the DSP following commands from the CPU. The signals then pass to a multiplexer 150, and are serialized before conversion from an analogue to a digital signal by the ADC. A programmable gain amplifier 160 matches the input signal to the range of the ADC 170. The output of the ADC 170 passes to the DSP 130. The DSP 130 processes the information to calculate the DC potential and its pattern on the ductal-epithelial or skin surface as well as over the region of suspicion. In addition the impedance at varying depth and response of the DC potential and impedance to different ECM concentrations of ions, drug, hormones, or other agent are used to estimate the probability of cancer. The results are then sent to the CPU 180 to give a test result 185.

Alternatively the signal interpretation may partly or completely take place in the CPU 180. An arbitrary waveform generator 190 or sine wave frequency generator will be used to send a composite waveform signal to the probe electrodes and tissue under test. The measured signal response (in the case of the composite wave form stimulus) may be deconvolved using FFT (Fast Fourier Transforms) in the DSP 130 or CPU 180 from which the impedance profile is measured under the different test conditions. An internal calibration reference 195 is used for internal calibration of the system for impedance measurements. DC calibration may be performed externally, calibrating the probe being utilized against an external reference electrolyte solution. As illustrated in FIG. 1, an overload sensor is provided between the reference probe or nipple electrodes 110 and the internal calibration reference 195.

Figure 2:
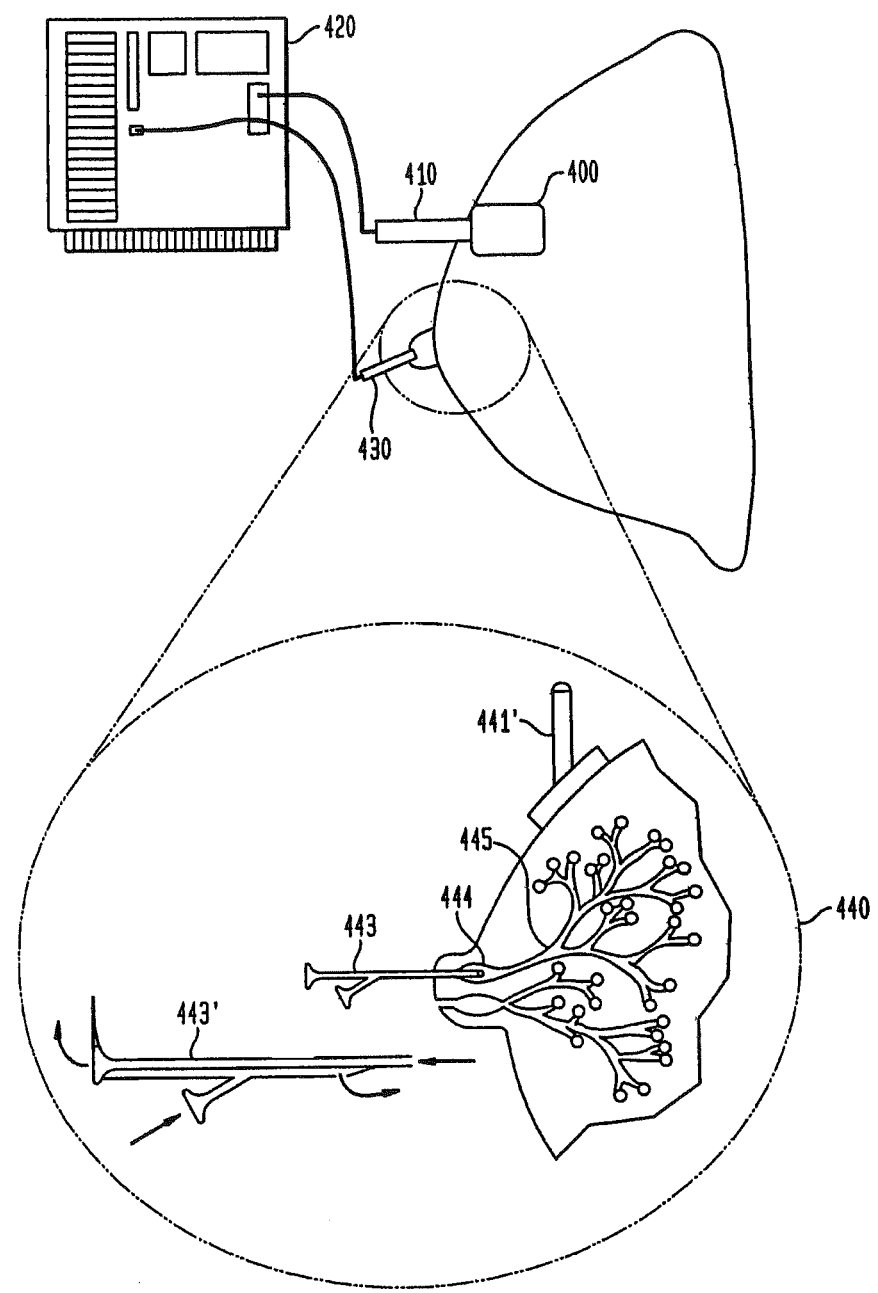
FIG. 2 illustrates an exemplary embodiment of a device suitable for use with systems and methods consistent with the present invention.

FIG. 2 includes a handheld probe 400, consistent with the present invention, which may be applied to the surface of the breast. The probe may include a handle 410. The probe 400 may be attached, either directly or indirectly using, for example, wireless technology, to a measurement device 420. The probe 400 may be referenced to an intravenous electrode, a skin surface electrode, other ground, nipple electrode, or ductal probe electrode within the duct or at the nipple orifice. In one embodiment, illustrated in FIG. 2, the reference is a nipple electrode or ductal probe 430, illustrated in greater detail at close-up 440. One advantage of this configuration is that DC electropotential and impedance can be measured between the nipple electrode 430 and the probe 400. The measurement is thus a combination of the DC potentials or/and impedance of the breast ductal epithelium, non-ductal breast-parenchyma, and the skin.

Referring to close-up 440, the ductal probe is inserted into one of several ductal orifices that open onto the surface of the nipple. Ductal probe 443 is shown within a ductal sinus 444, which drains a larger collecting duct 445. The handle 410 is illustrated in the closeup 440 at 441'.

Another advantage of using a nipple electrode is that a solution for irrigating the ductal system may be exchanged through the probe, permitting introduction of pharmacological and/or hormonal agents. As shown in magnified nipple probe 443, 443' fluid can be exchanged through a side port. Fluid may be infused into the duct and aspirated at the proximal end (away from the nipple) of the nipple probe. Different electrolyte solutions may be infused into the duct to measure altered permeability of the ductal epithelium to specific ions or the epithelium may be probed with different drugs to identify regions of abnormality. Estradiol, or other hormonal agents, may be infused into a breast duct to measure the abnormal electrical response associated with pre-malignant or malignant changes in the epithelium.

It should be understood that different configurations may also be used, such as a modified Sartorius cup that applies suction to the nipple. With this configuration, gentle suction is applied to a cup placed over the nipple. Small amounts of fluid within the large ducts and duct sinuses make contact with the electrolyte solution within the Sartorius cup, establishing electrical contact with the fluid filling the breast ducts. DC or AC measurements may then be made between the cup and a surface breast probe.

Figure 3:
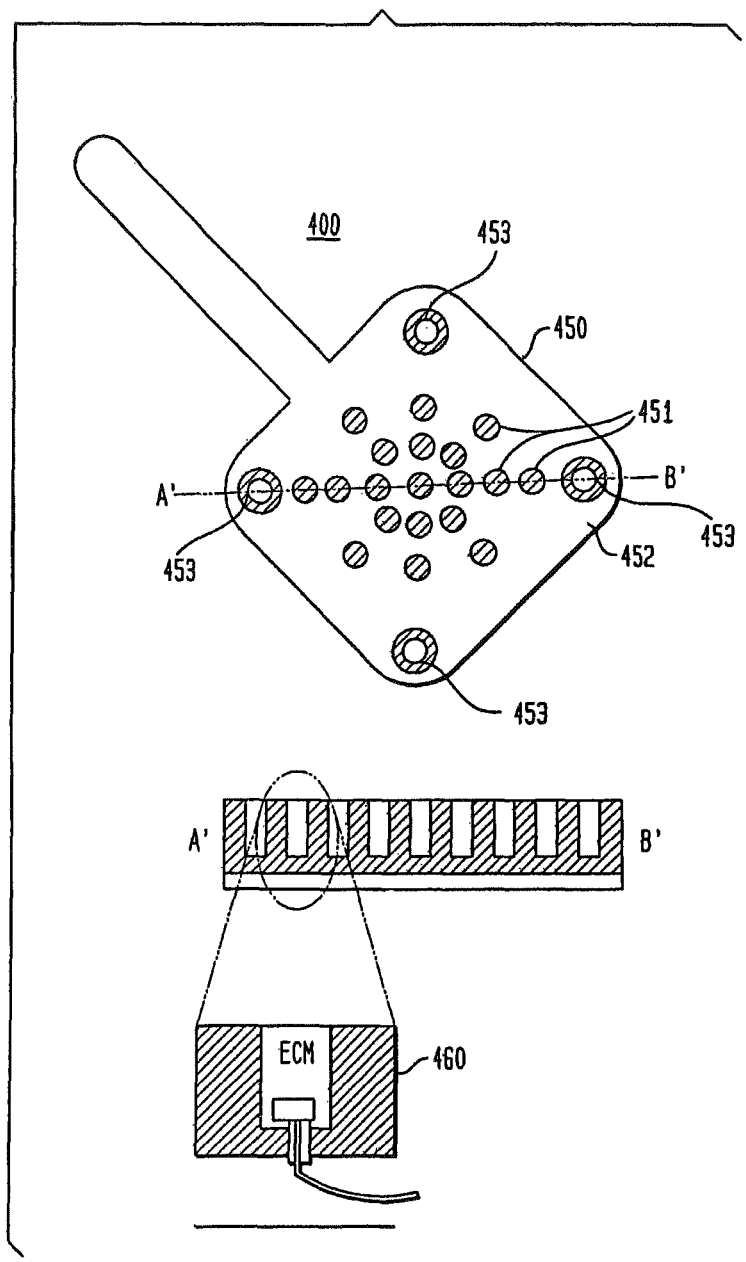
FIG. 3 illustrates an exemplary embodiment of a surface measurement probe suitable for use with systems and methods consistent with the present invention.

FIG. 3 illustrates the probe 400 of FIG. 2 in greater detail. The skin contact of the surface 450 is placed in contact with the breast. The surface electrodes 451 measure DC or AC voltages. The current passing electrodes 452 are used for impedance measurements. Probe 400 may also include one or more recessed wells containing one or more ECMs, illustrated at 460. Multiple sensor electrode arrays may be attached to the surface probe together with current passing electrodes. The individual electrodes may be recessed and ECMs with different composition may be used to pharmacologically, electrophysiologically, or hormonally probe the deeper tissues or epithelium under test. Spacing of the electrodes may be greater for the breast configuration than for other organ systems so that deeper tissue may be electrically probed and the impedance of the deeper tissue evaluated. This probe may either be placed passively in contact with the surface of the breast or held in place by pneumatic suction over the region of interest. Ports may be placed for the exchange of solutions or for fluid exchange and suction (not shown). Guard rings (not shown) may be incorporated to prevent cross-talk between electrodes and to force current from the contact surface into the breast. In this configuration there are four current passing electrodes [453] each positioned radially 90° apart. This permits current to be passed and the voltage response to be measured in perpendicular fields. The electrodes will be interfaced via electrical wire, or wireless technology, with the device described in FIG. 1 above.

Further embodiments of this technique may involve the use of spaced electrodes to probe different depths of the breast, and the use of hormones, drugs, and other agents to differentially alter the impedance and transepithelial potential from benign and malignant breast tissue, measured at the skin surface. This enables further improvements in diagnostic accuracy.

Figure 4:
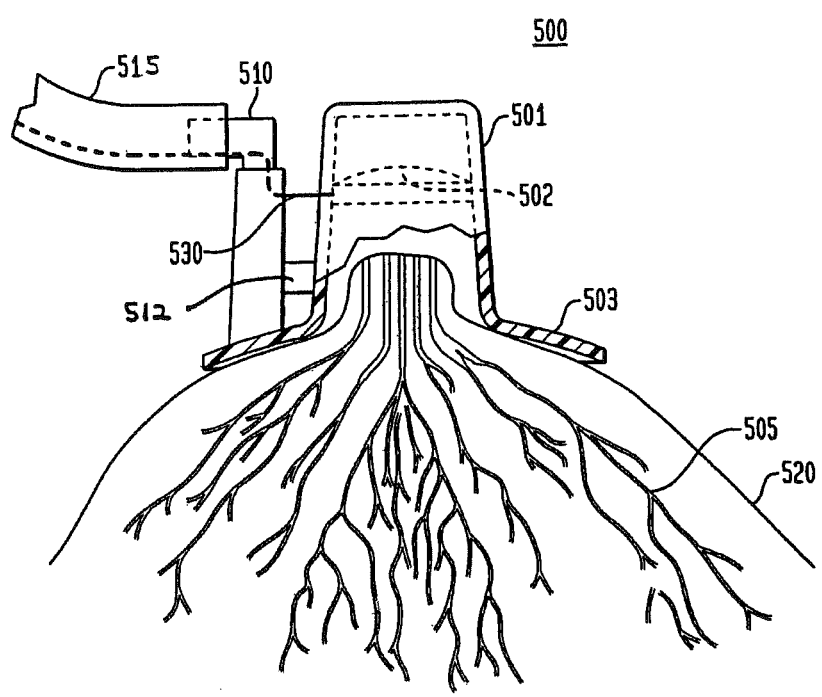
FIG. 4 illustrates an exemplary embodiment of a nipple electrode suitable for use with systems and methods consistent with the present invention.

FIG. 4 illustrates a nipple cup electrode [500] that may be used as a reference, current passing, voltage measuring or combination electrode [502]. In this configuration suction and fluid exchange is applied to the electrode housing [501] through a side port [510] connected by a flexible hose [515] to a suction device, aspirator or syringe (not shown). The flange [503] at the base of the cup is applied to the areola of the breast [520]. Pneumatic suction is applied through the side port and communicated to the housing by passage [512] so as to obtain a seal between the breast [520] and the nipple electrode [501]. Electrolyte solution is used to fill the cup and make electrical contact with the underlying ductal system. Fluid may be exchanged, or pharmacological and hormonal agents introduced, by applying alternating suction and injecting fluid or drugs into the cup through the side port. The pneumatic suction will open up the duct openings [505] either by itself or after preparation with alcohol or de-keratinizing agents to remove keratin plugs at the duct openings at the surface of the nipple. The nipple cup electrode [500] may be interfaced by means of an electrical connection [530] or by a wireless connection (not shown) with the devices illustrated in FIGS. 1-3 to obtain DC potential, AC impedance or combination measurements.

Figure 5:
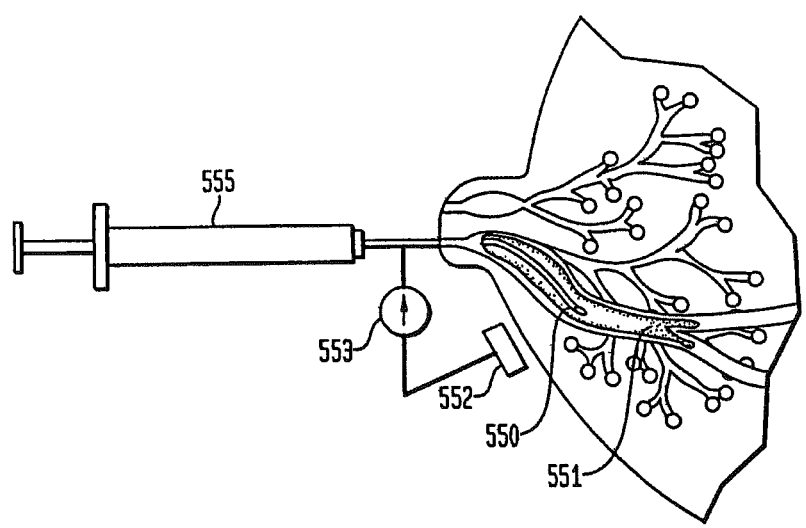
FIG. 5 illustrates an exemplary embodiment of a ductal electrode probe suitable for use with systems and methods consistent with the present invention.

FIG. 5 illustrates an alternative approach where an individual duct is probed with a flexible catheter electrode [550] attached to a syringe [555]. This may be used when a specific duct produces fluid and diagnosis is to be performed on the specific ductal system producing the fluid. In this configuration a saline filled syringe is connected to a flexible electrode [550], which is inserted into the duct [551]. Fluid may be exchanged, or drugs and hormones may be infused into the duct, through the catheter. An electrode within, or attached to the syringe makes electrical contact with the individual ductal system, and the surface probe electrodes [552] complete the circuit so that the DC potential, AC impedance or a combination of both may be measured across the ductal epithelium, skin and intervening breast parenchyma, as illustrated schematically by the gauge shown at [553], in combination with the systems described in FIGS. 1-3. Another approach would be to use a ductoscope in combination with a surface probe with the electrode(s) interfaced with the ductoscope.

Devices to measure the electrophysiological characteristics of tissue and the differences between normal and abnormal tissue may include those known in the art such as electrical meters, digital signal processors, volt meters, oscillators, signal processors, potentiometers, or any other device used to measure voltage, conductance, resistance or impedance.

DC potential is usually measured using a voltmeter, consisting of a galvanometer in series with a high resistance, and two electrodes (one working and one reference). Voltmeters may be analog or digital. Ideally these should have an extremely high input resistance to avoid current-draw. DC potential may also be measured with an oscilloscope.

Impedance may be measured using a number of approaches. Without limitation, examples include phase-lock amplifiers, which may be either digital or analog lock-in amplifiers. Pre-amplifiers may be used in conjunction with the lock-in amplifier to minimize stray currents to ground improving accuracy. Digital lock-in amplifiers are based on the multiplication of two sine waves, one being the signal carrying the amplitude-modulated information of interest, and the other being a reference signal with a specific frequency and phase. A signal generator can be used to produce the sine waves or composite signal to stimulate the tissue. Analog lock-in amplifiers contain a synchronous rectifier that includes a phase-sensitive detector (PSD) and a low-pass filter. Other approaches include the use of an impedance bridge with an oscillator to produce an AC sine wave. These devices when automated are referred to as LCR-meters and use an auto-balancing bridge technique. Constant current or constant voltage current sources may be used. In one preferred embodiment, a constant current source is used. Rather than an oscillator with a fixed frequency signal a signal generator, which produces, superimposed sine waves may be used.

The tissue response is deconvolved using fast Fourier transforms or other techniques. Bipolar, tripolar or tetrapolar current and voltage electrodes may be used to make measurements. In one preferred embodiment tetrapolar electrode configurations are employed to avoid inaccuracies that are introduced due to electrode polarization and electrode-tissue impedance errors. Rather than impedance, current density may be measured using an array of electrodes at the epithelial or skin surface. Impedance may also be measured using electromagnetic induction without the need for electrode contact with the skin or epithelium.

In order to process large amounts of data, the methods of the present invention could be implemented by software on computer readable medium and executed by computerized equipment or central processor units.

EXAMPLE 1

Breast Cancer

As mentioned above, impedance and DC electrical potential have been used separately at the skin's surface to diagnose breast cancer. Neither of these methods measures the ductal transepithelial DC or AC electrical properties of the breast. This significantly reduces the accuracy of the approach, because the origins of breast cancer are within the ductal epithelium, and not the surrounding breast stroma. Accuracy is further improved when the transepithelial measurements of impedance and DC potential are combined. The use of pharmacological and/or hormonal agents in combination with impedance or DC electrical potential measurements, provide a more effective method for detecting abnormal pre-cancerous or cancerous breast tissue.

Breast cancer develops within a background of disordered proliferation, which primarily affects the terminal ductal lobular units (TDLUs). The TDLUs are lined by epithelial cells, which maintain a TEP (transepithelial potential). In regions of up-regulated proliferation, the ducts are depolarized. The depolarization of ducts under the skin surface results in skin depolarization. The depolarization is significantly attenuated compared to that which is observed using a transepithelial ductal approach, as opposed to a non-transepithelial skin surface approach such as disclosed in U.S. Pat. Nos. 6,351,666; 5,678,547; 4,955,383. When a tumor develops in a region of up-regulated proliferation, the overlying breast skin becomes further depolarized compared with other regions of the breast and the impedance of the cancerous breast tissue decreases. The changes in ductal epithelial impedance are not measured using existing technologies resulting in a diminution in accuracy. Alterations in TEP and impedance occur under the influence of hormones and menstrual cycle.

For example, the electrophysiological response of breast tissue to 17-β-estradiol has been observed to be different in pre-cancerous or cancerous epithelium than in normal breast epithelium. In one method of the present invention, estradiol is introduced directly into the duct or systemically following sublingual administration of 17-β-estradiol (4 mg). This agent produces a rapid response, which peaks at approximately 20 minutes. The electrophysiological response depends, in part, on the stage of the patient's menstrual cycle, as well as the condition of the breast tissue. Specifically, in normal breast tissue, a rise in TEP will occur during the follicular (or early) phase. In pre-cancerous or cancerous tissue, this response is abrogated. Post-menopausal women at risk for breast cancer may have an exaggerated TEP response to estradiol because of up-regulated estrogen receptors on epithelial cell surfaces.

Furthermore, estrogen, progesterone, prolactin, corticosteroids, tamoxifen or metabolites, (all of which alter the ion transport characteristics of ductal epithelium depending on its premalignant, malignant and functional state), thereof may be introduced either orally, intravenously, transcutaneously, or by intraductal installation.

In one embodiment of the present invention, breast or other cancers may be diagnosed by examining the basal conductance state of the paracellular pathway of the epithelium. For example, in the breast, a substance known to affect the conductance of the tight junctions may be infused into the duct, or administered by other mean, and the transepithelial impedance and/or the DC potential of the breast is measured, before and after the administration of the agent, using a combination of surface, nipple, ductal or other electrodes. The difference in the transepithelial electrical response of the tight junctions to the agent in normal compared to pre-malignant or malignant breast epithelium is then is used to diagnose the presence or absence of malignancy.

In another embodiment, the electrodes are placed over the suspicious region and the passive DC potential is measured. Then AC impedance measurements are made as discussed below. The variable impedance properties of the overlying skin may attenuate or increase the measured DC surface electropotentials. Alternatively, impedance measurements at different frequencies may initially include a superimposed continuous sine wave on top of an applied DC voltage. Phase, DC voltage and AC voltage will be measured. The resistance of the skin or other epithelium at AC and a different resistance at DC are measured. Under DC conditions since there is no phase shift, it is possible to measure the transepithelial potential at the surface. The capacitive properties of the skin may allow the underlying breast epithelial and tumor potential to be measured at the skin surface.

Once the ECM results in "wetting" of the skin surface there is pseudo-exponential decay in the skin surface potential using the above referenced approach. Ions in the ECM diffuse through the skin and make it more conductive, particularly because of changes in the skin parallel resistance. The time constant for this decay is inversely proportional to the concentration and ionic strength of the gel. Once the skin is rendered more conductive by the ECM the capacitive coupling of the surface to the underlying potential of the tumor or the surrounding epithelium is lost so that the measured potential now reflects an offset and diffusion potential at the electrode-ECM-skin interfaces.

Figure 6:
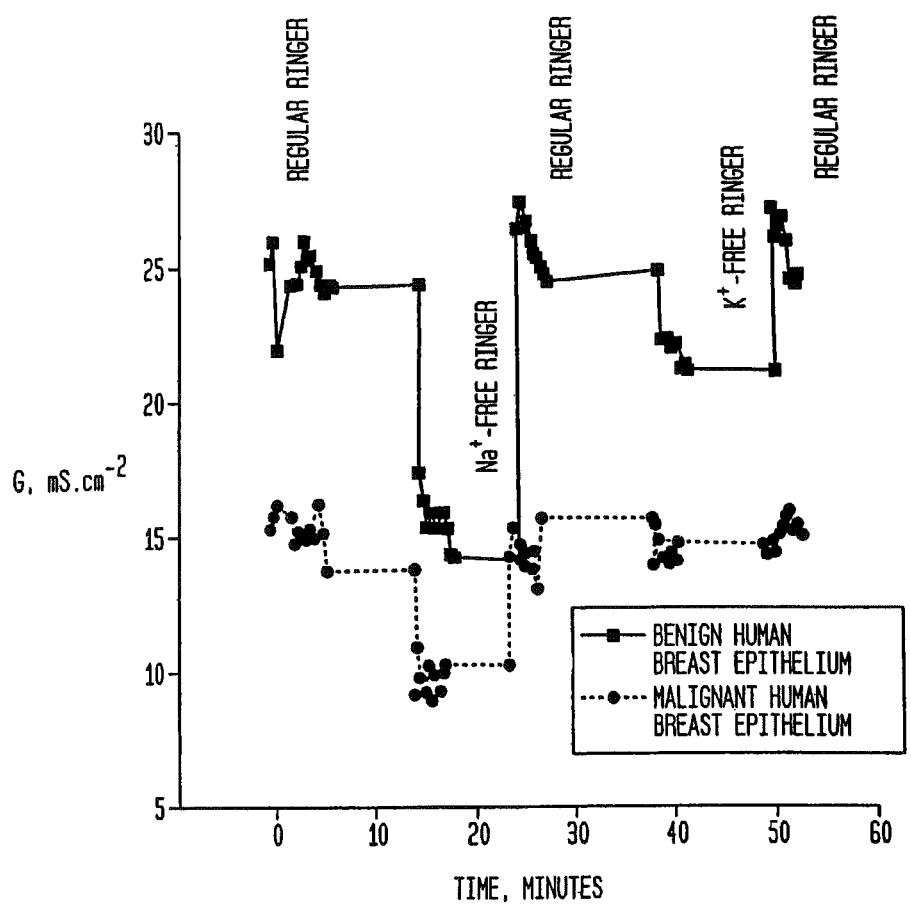
FIG. 6 illustrates varying ionic content and the effect on transepithelial conductance in human breast epithelium.

FIG. 6 demonstrates the effect of varying the ionic content of the bathing Ringers solution on transepithelial conductance. The human breast epithelial cells were grown as monolayers on Millipore filters and grew to confluence in 7 to 10 days. The epithelia were then mounted in modified Ussing chambers and the DC conductances were measured using a voltage clamp. The conductance was measured by passing a 2 µA current pulse for 200 milliseconds and measuring the DC voltage response and calculating the transepithelial conductance (y-axis), and plotting it against time (x-axis). The conductance was measured first in standard Ringer solution, then in a sodium-free Ringer, then returned to standard Ringer, then in a potassium-free Ringer and finally returning to standard Ringer solution while maintaining normal osmolality during the studies.

The upper plot (filled squares and solid line) demonstrates the conductance of benign human breast epithelia grown as a monolayer. The conductance is higher in the benign epithelial cells. The $Na^+$ and $K^+$ components of conductance are approximately, 10 and 5 $mS \cdot cm^{-2}$ respectively.

The lower plot (filled circles and dotted line) demonstrates the conductance of malignant human breast epithelia grown as a monolayer. The conductance is significantly lower in the malignant epithelial cells. The $Na^+$ and $K^+$ components of conductance are approximately, 4 and 1 $mS \cdot cm^{-2}$ respectively.

In malignant tumors as opposed to monolayers of malignant epithelial cells, the tight junction between cells break down and the tumor becomes more conductive than either benign or malignant epithelial monolayers. This observation may be exploited in the diagnosis of breast cancer. The lower conductance of the epithelium around a developing tumor, together with a region of high conductance at the site of the malignancy, may be used to more accurately diagnose breast cancer. Using electrodes with ECMs with different ionic composition will permit the specific ionic conductances to be used in cancer diagnosis. For example a high conductance region with a surrounding area of low K-conductance is indicative of breast cancer; a high conductance area with a surrounding region of normal conductance may be more indicative of fibrocystic disease (a benign process).

Figure 7:
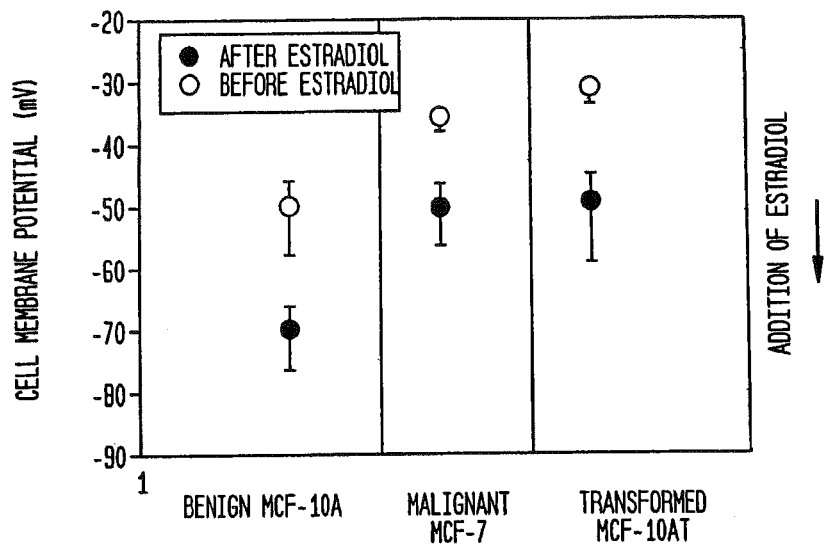
FIG. 7 illustrates measurements of cell membrane potential in human breast epithelial cells.

FIG. 7 demonstrates measurements of cell membrane potential (ψ) in human breast epithelial cells. Measurements were made using a potentiometric fluorescent probe, and ratiometric measurements, which are calibrated using valinomycin and $[K^+]$-gradients. ψs were measured in the presence (closed circles) and absence (open circles) of estradiol (the active metabolite of estrogen). Each symbol is the mean measurement. The upper error bar is the standard error of the mean, and the lower error bar is the 95% confidence level for the observations. The addition of estrogen to cultured breast epithelial cells results in an instantaneous increase in ψ (data not shown) as well as the transepithelial potential see FIG. 8. Transepithelial potential ($V_T$) of an epithelium is the sum of the apical (luminal) cell membrane potential ($V_A$) and the basolateral (abluminal) cell membrane potential ($V_{BL}$). Therefore $V_T = V_A + V_{BL}$ (changes in $V_A$ and/or $V_{BL}$ will therefore alter $V_T$ or transepithelial potential).

FIG. 7 demonstrates that benign breast epithelial cells have a ψ of approximately −50 mV in the absence of estradiol and −70 mV when estradiol is added to the culture media. Malignant and transformed cells have a ψ of between −31 and −35 mV in the absence of estradiol and approximately 50 mV when estradiol is present in the culture medium.

The difference in the electrical properties may be exploited to diagnose breast cancer in vivo. Surface electropotential measurements are a combination of the transepithelial potential, tumor potential and overlying skin potential. Physiological doses of estradiol may be administered to the patient to increase ψ and the sustained effect of estradiol results in an increase in transepithelial potential and tumor potential measured as an increase in surface electropotential. The increase following sustained exposure (as opposed to the instantaneous response) is less in malignant than benign breast tissue.

Figure 8:
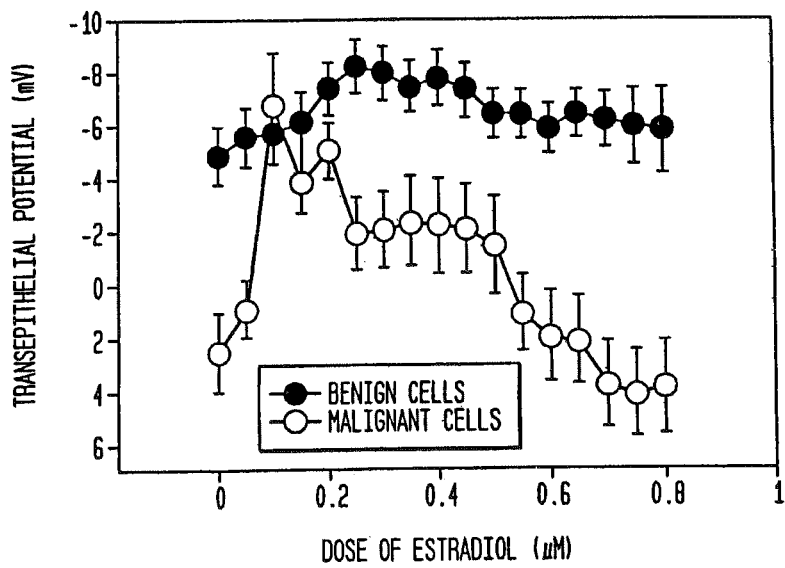
FIG. 8 illustrates the effect of increasing estradiol concentrations on the transepithelial potential in benign and malignant breast epithelia.

It should be noted that the instantaneous response, illustrated in FIG. 8, is greater in malignant epithelia, whereas the chronic or sustained exposure to estradiol results in a lower increase in TEP (transepithelial electropotential) in malignant cells. Concurrent measurement of surface electropotential and impedance allow the more accurate diagnosis of cancer. FIG. 8 demonstrates the instantaneous effect of increasing doses of estradiol on the transepithelial potential (TEP) of benign and malignant human breast epithelial cells. The cells were grown as monolayers on Millipore filters and grew to confluence in 7 to 10 days. The epithelia were then mounted in modified Ussing chambers and the TEP was measured using a voltage clamp. Increasing doses of estradiol between 0 and 0.8 µM were added (x-axis). The transepithelial potential was measured after each addition and the TEP was measured (y-axis).

The different dose response is apparent for benign and malignant epithelia. Malignant epithelia have a lower TEP but undergo an instantaneous increase in TEP of approximately 9 mV (becomes more electronegative and reaches a level of <−6 mV) after exposure to only 0.1 µM estradiol and then depolarize to approximately −2 mV with increasing doses of estradiol up to about 0.5 µM. Benign epithelia have a lesser response to increasing doses of estradiol and do not peak until almost 0.3 µM and then remain persistently elevated (higher electro negativity), unlike the malignant epithelia, with increasing doses of estradiol.

This difference in dose response may be exploited to diagnose breast cancer. Estradiol, or other estrogens, at a low dose will be administered systemically, transcutaneously, intraductally, or by other route. The instantaneous response of the surface electropotential and/or impedance may then be used to diagnose breast cancer with improved accuracy over existing diagnostic modalities using impedance or DC measurement alone.

Figure 9:
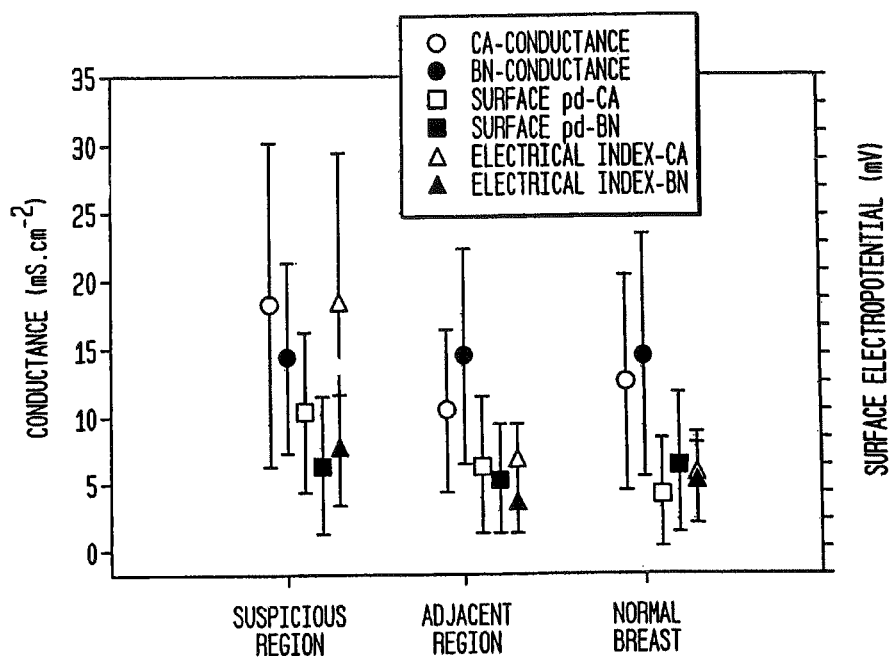
FIG. 9 illustrates conductance and the electropotential measurements made over the surface of the breast in women with and without breast cancer.

FIG. 9 shows conductance measurements made at 2000 Hz at the surface of the breast. At this frequency the influence of the overlying skin impedance is less. There is still however some variable component of skin impedance, which results in significant variability of the measurement as evidenced by the overlapping error bars. Each symbol represents the median measurement with error bars the standard deviation of the mean.

Open symbols represent measurements made in patients with a biopsy proven malignancy, while closed symbols represent measurements made in patients whose subsequent biopsy proved to be a benign process such as fibrocystic disease. Malignant lesions are often associated with surrounding breast epithelium that demonstrates Up-regulated proliferation. These regions ("adjacent region") are depolarized and may have a lower conductance than either over the region of malignancy. This decreased conductance may be because of decreased $K^+$-conductance of the adjacent and pre-malignant epithelium as I have observed in human colon.

Each of the three groups of symbols represents measurements from over a suspicious lesion or region, then the adjacent region, and then over normal breast in an uninvolved quadrant of the breast. The first two symbols (circles) in each of the three groups are impedance measurements where the median value is plotted against the left y-axis as conductance in $mS.cm^{-2}$. The second two symbols (squares) is the surface electrical potential measured in mV and plotted against the right y-axis; each division equals 5 mV. The third two symbols (triangles) are the electrical index for benign and malignant lesions and are in arbitrary units and are derived from the conductance and surface potential measurement. It is immediately apparent that there is less overlap in the error bars (standard deviation of the mean). Therefore breast cancer can be more accurately diagnosed using a combination of surface potential measurement and AC-impedance measurements. Further enhancements of this technique will involve the use of spaced electrodes to probe different depths of the breast, and the use of the hormones, drugs and other agents to differentially alter the impedance and transepithelial potential from benign and malignant breast tissue, and measured at the skin or duct surface. This will enable further improvements in diagnostic accuracy.

Figure 10:
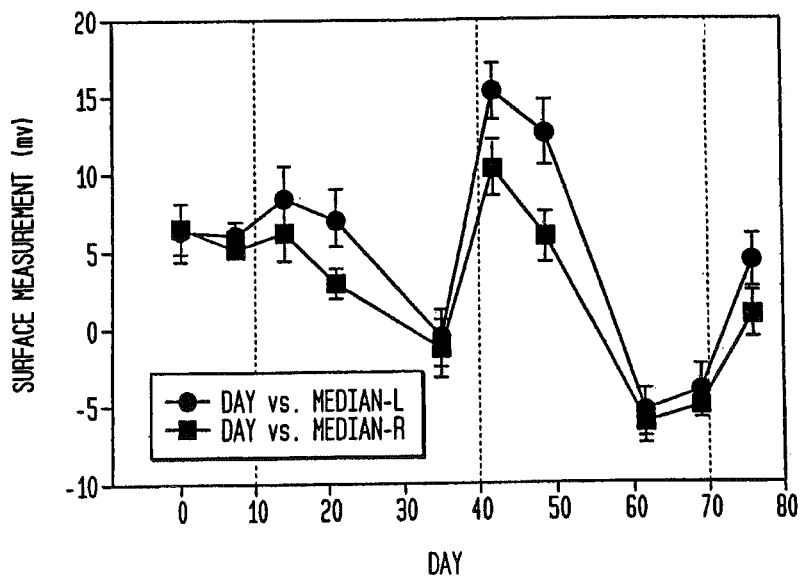
FIG. 10 illustrates the measurement of electropotentials at the surface of the breast, and variation of the measurement during menstrual cycle.

It should be understood that the surface potential measurement of breast tissue varies based on the position of the woman in her menstrual cycle. FIG. 10 illustrates this variance. This figure demonstrates electropotential measurements taken over the surface of each breast at 8 different locations with an array of 8 electrodes on each breast referenced to an electrode on the skin of the upper abdomen. Measurements are taken with error bars equal to the standard error of the mean. Filled circles and filled squares represent the median value from the left and right breast respectively. The vertical dotted line is the first day of each menstrual cycle.

It can be seen that the median values for each breast tend to track one another with lower values in the first half of menstrual cycle (follicular phase) and higher values in the latter part of cycle (luteal phase). Although the measured electrical values are not completely superimposed, because of other factors affecting the electropotential of the breast, it can be seen that the lowest levels of electropotential are observed 8-10 days before menstruation and the rise to the highest levels around the time of menstruation. This may be because estradiol levels are higher in the second part of menstrual cycle and directly affect breast surface electropotential.

The cyclical pattern of electropotential activity when a breast cancer or proliferative lesion is present is quite different. Similarly higher levels of surface electropotential are observed when measurements were made in the afternoon compared with the morning. This information can be exploited in a number of different ways. Measurement of the surface potential and impedance at different times during cycle enables a more accurate diagnosis because of a different cyclical change in surface electropotential (i.e., the peak to peak change in potential is less over a malignant region, relative to normal areas of the breast). Secondly, estradiol or another agent that changes the electropotential of the breast may be administered systemically, topically (transdermal), intraductally or by other means, and the drug or hormone-induced change in surface potential may be used as a provocative test to diagnose breast cancer.

Figure 11:
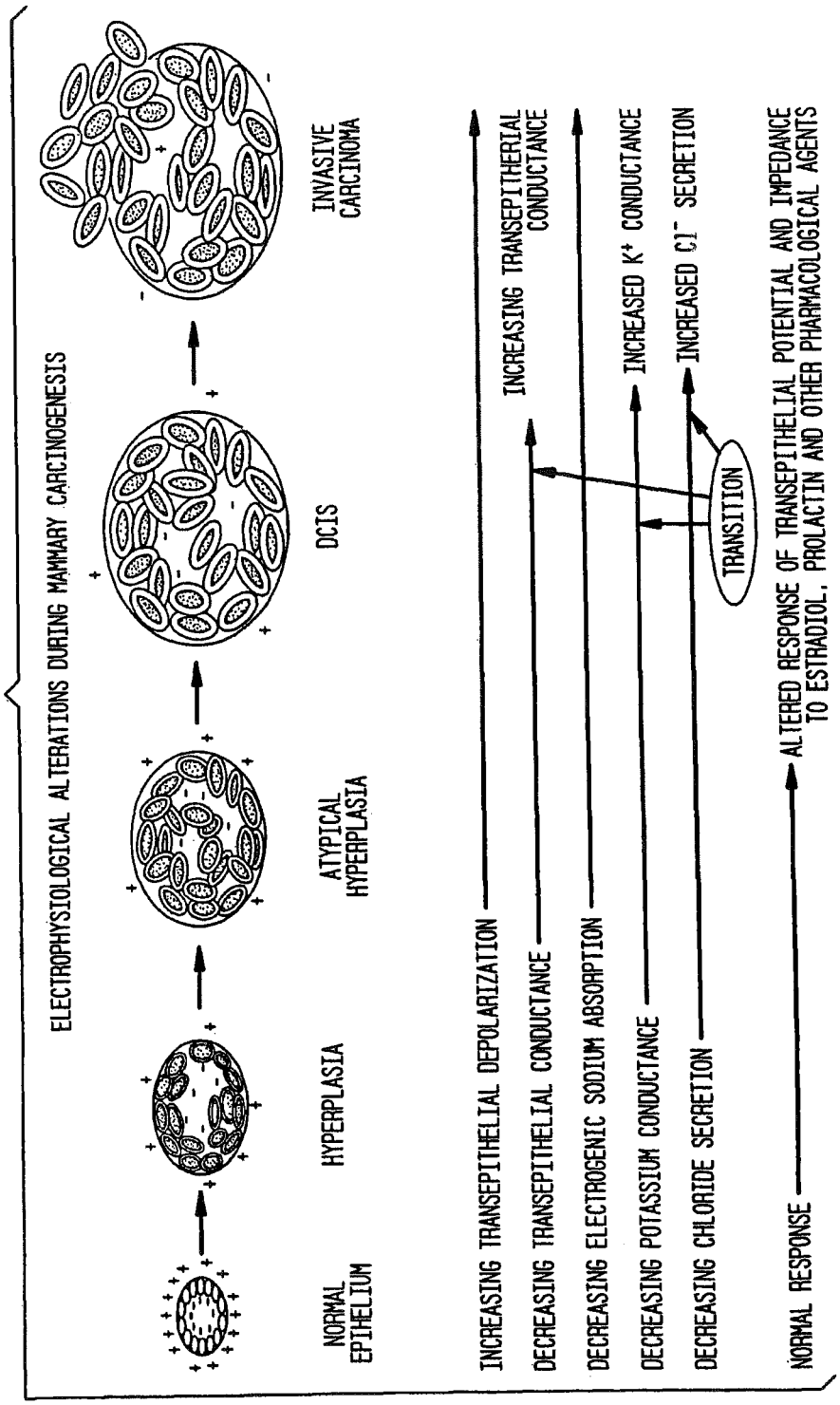
FIG. 11 illustrates electrophysiological changes that occur within the ductal epithelium during the development of breast cancer.

FIG. 11 is a diagram illustrating the histological and electrophysiological changes that occur during the development of breast cancer. The continuum from normal ductal epithelium, through hyperplasia, atypical hyperplasia, ductal carcinoma in situ (DCIS), to invasive breast cancer is thought to take 10 to 15 years. Some of the steps may be skipped although usually a breast cancer develops within a background of disordered ductal proliferation. The normal duct maintains a transepithelial potential (inside of duct negatively charged), which depolarizes and impedance, which increases during the development of cancer. Once an invasive breast cancer develops the impedance decreases with loss of tight junction integrity, and conductance through the tumor is enhanced. The disordered ducts have altered electrophysiogical and ion transport properties. These properties are illustrated in the lower aspect of FIG. 11. These electrophysiological and transport alterations will be exploited to diagnose cancer and premalignant changes in the breast.

In these ways breast cancer can be more accurately diagnosed using transepithelial measurements of potential, or impedance, or a combination of transepithelial surface potential measurement, AC-impedance measurements and pharmacological manipulations.

EXAMPLE 2

Chemopreventative and Therapeutic Use

In addition to the ionic, pharmacologic, and hormonal agents described above, the system and method of the present invention may be used with cancer preventative and therapeutic agents and treatments. Specifically, electrical measurement of altered structure and function provides a method for evaluating a patient's response to the drugs without requiring a biopsy and without waiting for the cancer to further develop. Patients who respond to a given chemopreventative or therapeutic agent would likely show restoration of epithelial function to a more normal state. Patients who do not respond would show minimal change or may even demonstrate progression to a more advanced stage of the disease. This system and method, thus, may be used by either clinicians or drug companies in assessing drug response or by clinicians in monitoring the progress of a patient's disease and treatment, or monitoring the process of carcinogenesis (cancer development), before an overt malignancy has fully developed.

EXAMPLE 3

Electrophysiological Changes in other Epithelia

Figure 12:
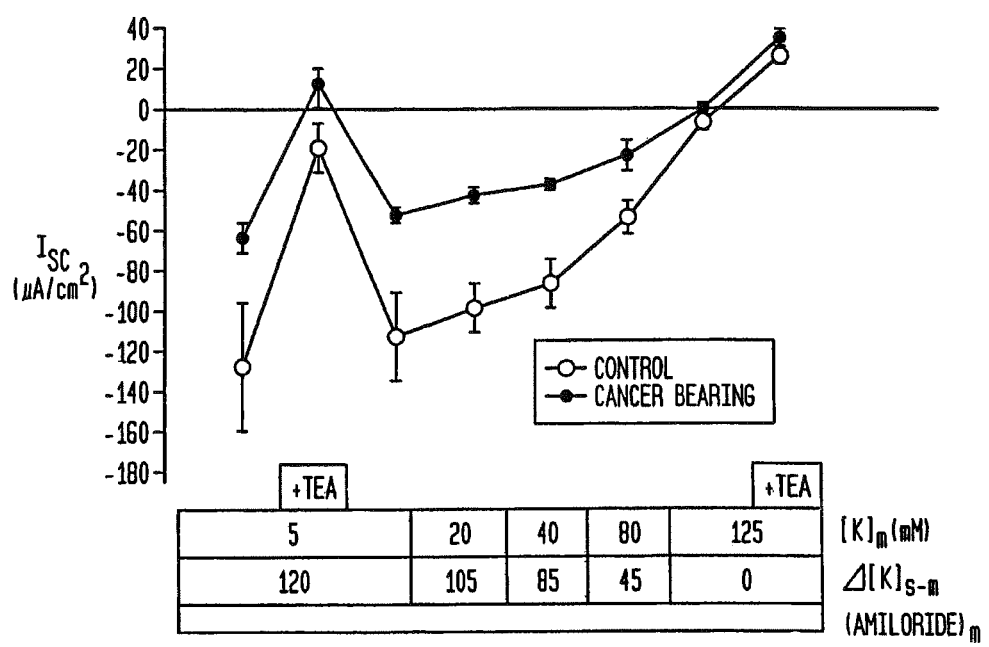
FIG. 12 illustrates changes in the short circuit current of human epithelium exposed to a potassium channel blocker (TEA) or varying concentrations of potassium.
Figure 13:
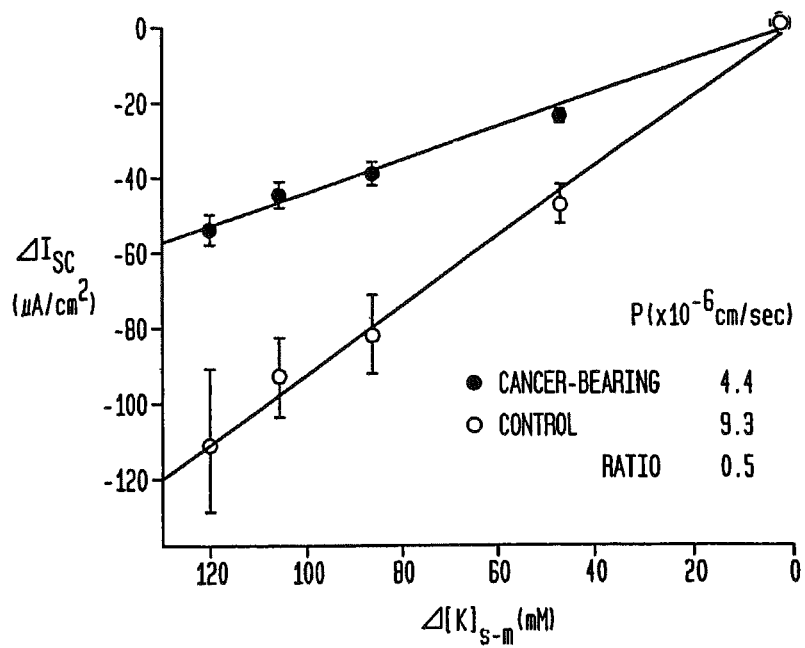
FIG. 13 illustrates how the information obtained in FIG. 12 may be used to plot the potassium gradient against the change in short circuit current.

The examples illustrated by FIGS. 12 and 13 were performed in human colon specimen removed at the time of surgery. Based on in vitro studies in breast epithelial tissues, similar changes in human ductal epithelium that can be measured in vivo are expected.

FIG. 12 demonstrates the short circuit current ($I_{SC}$) of human colonic epithelium ex-vivo. The figure demonstrates the time course along the x-axis while varying the potassium gradient across the tissue. The potassium permeability of the apical membrane of human colonic mucosa ($P^K_a$) was determined in surgical specimens of controls and grossly normal-appearing mucosa obtained 10-30 cm proximal to colorectal adenocarcinomas. The mucosa was mounted in Ussing chambers and the basolateral membrane resistance and voltage were nullified by elevating the $K^+$ in the serosal bathing solution. The apical sodium ($Na^+$) conductance was blocked with 0.1 mM amiloride. This protocol reduces the equivalent circuit model of the epithelium to an apical membrane conductance and electromotive force in parallel with the paracellular pathway as has been verified by microelectrode studies. Increasing serosal $K^+$ caused the $I_{sc}$ to become negative (−140 μA/cm2) in normal colon after which 30 mM mucosal TEA caused an abrupt increase in $I_{sc}$ corresponding to block of apical $K^+$ channels. In cancer-bearing colon the reduction in $I_{sc}$ is to −65 μA/cm². The serosal bath was remained constant at 125 mM [K].

FIG. 13 demonstrates that ΔIsc, determined with respect to the $I_{sc}$ at 125 mM mucosal K, is a linear function of the concentration gradient, Δ[K]. Because the voltage across the apical membrane is zero under these conditions and the paracellular pathway is nonselective, the $P^K_a$ (apical potassium permeability) can be calculated using the Fick equation i.e., $I_{sc}=F \cdot P^K_a \cdot \Delta[K]$ where F is the Faraday constant and Δ[K] is the concentration difference for $K^+$ across the epithelium. FIG. 13 demonstrates mean±sem values for $I_{sc}$ in both normal and premalignant human distal colon. The apical $K^+$ permeability of controls was $9.34 \times 10^{-6}$ cm/sec and this was significantly reduced by 50% in premalignant human mucosa to $4.45 \times 10^{-6}$ cm/sec. $P^K_a$ could also be calculated for the change in $I_{sc}$ when the $K^+$ channels were blocked with TEA, assuming complete block. This resulted in somewhat lower values of $6.4 \times 10^{-6}$ cm/sec and $3.8 \times 10^{-6}$ cm/sec corresponding to a 40% reduction in $P^K_a$.

These observations show that there is a field change in the $K^+$ permeability and conductance of human colon, during the development of cancer. Similar results are expected in breast ductal epithelium. Impedance measurements, and/or DC measurement using electrodes with different potassium gradients together with specific drugs, such as amiloride to block the contributions of electrogenic $Na^+$ transport; to the electrical properties of the breast may be useful to diagnose breast cancer. Amiloride may be introduced through the breast duct and then the $K^+$-concentration varied in the ECM used in the nipple electrode or irrigated into the duct to measure the reduced potassium permeability observed in the surrounding breast ductal epithelium (with atypical ductal hyperplasia or early DCIS), or increased permeability in the region of the developing invasive breast cancer.

Devices for Use with the Present Invention

A number of variations are possible for devices to be used with the present invention. Further, as noted above, within a device design, there are a number of aspects that may be varied. These variations, and others, are described below.

One embodiment of a probe or other device for use in the present invention includes a plurality of miniaturized electrodes in recessed wells. Surface recording and initial electronic processing, such as filtering, may be performed by disposable commercially-available silicon chips. Each ECM solution or agent may be specific to the individual electrode and reservoir on the chip. Thus, for one measurement, a particular set of electrodes would be used. For another measurement, for example, at a different ionic concentration, a different set of electrodes would be used. While this produces some variations, as the electrodes for one measurement are not located at the same points as for another, this system provides generally reliable results.

An alternative approach is to use fewer electrodes and use a flow-through or microfluidic system to change solutions and drugs. Specifically, solutions or agents are changed by passing small amounts of electrical current to move solution or agent through channels and out through pores in the surface of the device. In this embodiment, the electrode remains in contact with the same region of the surface of the breast, thus eliminating region-to-region variation in measurement. This approach requires time for equilibration between different solutions. In detecting the presence of abnormal pre-cancerous or cancerous breast tissue, a hand-held probe is provided for obtaining surface measurements at the skin. The probe may include electrodes for passing current as well as for measuring. An impedance measurement may be taken between the nipple cup electrode and the hand-held probe, between a nipple cup electrode and adhesive skin electrodes, between electrodes on a miniature ductoscope, between electrodes on a ductoscope and the skin surface electrodes, or may be taken between electrodes on the hand-held probe. After taking initial DC measurements, a wetting/permeabilizing agent may be introduced to reduce skin impedance. The agent may be introduced using a microfluidic approach, as described above, to move fluid to the surface of the electrodes. Alternatively, surface electrodes that just penetrate the stratum corneum may be used to decrease impedance.

Fluids for use with the present inventions could include various electrolyte solutions such as physiologic saline (e.g. Ringers) with or without pharmacological agents. One preferable electrolyte solution to infuse into the ductal system will represent a physiological Ringer solution. Typically this consists of NaCl 6 g, KCl 0.075 g, $CaCl_2$ 0.1 g, $NaHCO_3$ 0.1 g, and smaller concentrations of sodium hyper and hypophosphate at a physiological pH of 7.4. Other electrolyte solution may be used were the electrolyte comprises approximately 1% of the volume of the solute. Hypertonic or hypotonic solutions that are greater or less than 1% may be used in provocative testing of the epithelium and/or tumor. The concentration of Na, K and Cl will be adjusted under different conditions to evaluate the conductance and permeability of the epithelium. Different pharmacological agents such as amiloride (to block electrogenic sodium absorption), Forskolin (or similar drugs to raise cyclic-AMP) and hormones such as prolactin or estradiol can also be infused with the Ringer solution to examine the electrophysiological response of the epithelium and tumor to these agents. Similarly, the calcium concentration of the infusate will be varied to alter the tight junction permeability and measure the electrophysiological response of the epithelium to this manipulation. Dexamethasone may be infused to decrease the permeability of the tight junctions, and the electrophysiological response will be measured.

Although specific examples have been given of drugs and hormones that may be used in "challenge" testing of the epithelium and tumor, any agonist or antagonist of specific ionic transport, or tight-junctional integrity, known to be affected during carcinogenesis may be used, particularly when it is known to influence the electrophysiological properties of the epithelium or tumor.

Regardless of the configuration of the device, a signal is used to measure either the ductal transepithelial potential by itself, or the transepithelial impedance. These two measurements may then be combined to characterize the electrical properties of the epithelium associated with a developing abnormality of the breast, and are then compared with uninvolved areas of the same or opposite breast. Surface electropotential measurements and impedance measurements are then made to characterize the non-transepithelial electrical properties of the breast. These measurements involve DC potential measurements where the surface potential is referenced to an electrode that is not in contact directly, or indirectly through an ECM, with the duct lumen. Impedance measurements are similarly made between surface electrodes or a surface electrode and a reference electrode not in contact directly or indirectly (through an ECM) with the ductal lumen. These measurements are then compared and combined with the transepithelial electrical measurements to further characterize the breast tissue.

Furthermore an understanding of the electrophysiological basis of the altered impedance or DC potential permits more accurate diagnosis. For example impedance or DC potential may increase or decrease because of several factors. Increased stromal density of the breast may alter its impedance. This is a non-specific change, which may not have bearing on the probability of malignancy. On the other hand, a decrease in the potassium permeability of the epithelia around a developing malignancy would increase impedance and would be more likely associated with a developing cancer than a non-specific impedance change. Additional information is obtained from my method by probing the tissue to different depths using spaced voltage-sensing electrodes. The use of electrophysiological, pharmacological and hormonal manipulations to alter DC potential and/or DC potential differentially in normal compared to cancer-prone, pre-malignant or malignant tissue is another significant difference, which enhances the diagnostic accuracy of my invention over the above referenced ones.

Although the use of a nipple cup electrode has been described in this application for use in breast cancer diagnosis, a cup electrode may be used in other organs where the epithelium may be difficult to access endoscopically, or an endoscopic approach is not desired. An example would be the pancreatic and bile ducts, which join and open at the ampulla of Vater within the second part of the duodenum. Bile duct tumors develop from the endothelial lining of the bile duct, (i.e., cholangiocarcinomas, or the epithelial lining of the pancreatic duct, i.e., pancreatic carcinomas). The ampulla may be accessed endoscopically and a cup electrode applied by suction to the ampulla. Physiological saline can be infused into the ducts and then a transepithelial potential and impedance could be measured intraoperatively to identify the region of tumor in the pancreatic, or bile duct using a second electrode placed on the peritoneal surface of the pancreas or bile duct. Alternatively, the peritoneal surface electrode may be replaced by a skin surface, or intravenous electrode when used in a minimally or non-invasive manner.

Drugs may be infused though the cup electrode as a provocative test and described for breast. Secretin for example, stimulates bicarbonate secretion by the pancreatic ducts. This response may be abrogated by changes in the epithelium associated with pancreatic carcinoma. The distribution of muscarinic receptors, particularly M1 and M3, may be altered in the epithelium during pancreatic carcinogenesis. Therefore specific muscarinic agonists (cholinomimetic choline esters and natural alkaloids) and antagonists (atropine, Pirenzepine (M1), Darifenacin (M3)) may be used to elicit a particular electrophysiological response due to chloride secretion in ductal epithelium associated with pancreatic cancer. Similar approaches may be used in the intra and extrahepatic bile ducts to diagnose liver cancer.

Prostatic cancer may be diagnosed using a urethral cup electrode applied to the external urethral meatus. Physiological saline is infused into the urethra. Direct electrical connection is established with the prostatic ductal and acinar epithelium via prostatic ducts that open into the prostatic urethra. A surface electrode may then be placed per rectum onto the surface of the prostate and electrophysiological measurements may be made in a transepithelial fashion as described in the breast. Similarly, provocative tests may be performed with drugs and hormones that differentially affect the electrophysiological characteristics of abnormal prostatic epithelium when compared to normal prostatic tissue.

Endometrial cancer may be diagnosed with an electrode cup placed on the uterine cervix. Physiological saline may be infused through the cervical canal to make electrical contact with the endometrium. Electrophysiological measurements may be made with a reference electrode, placed on the skin, intravenously or at a suitable reference point. Alternatively, this approach may be used during surgery where the cervical cup electrode is used in conjunction with a reference electrode used on the peritoneal or outside surface of the uterus.

Salivary gland tumors open through small ducts into the oral cavity. For example in the parotid gland, Stensen's duct opens inside the mouth opposite the second upper molar tooth. A cup electrode may be used over the opening of the duct inside the mouth. Physiological saline is infused into the duct and electrical contact is thus established with the ductal epithelium of the salivary gland. A surface electrode is then used over the skin surface of the gland and electrical measurements are used to establish the diagnosis of cancer.

Although specific examples have been given above, this technique may be used to diagnose any tumor, where endoscopic access to the epithelium is not possible or desired. The application of physiological saline via a cup or short catheter may be used for example in the bowel or other organ system where electrical contact with the epithelium permits a transepithelial electrophysiological measurement to be made without resorting to endoscopic electrode placement. The second electrode is then used to externally scan the organ for the presence of a tumor or abnormal epithelium. Since the physiological saline acts as an electrode in direct contact with the epithelium this approach simplifies the approach to electrophysiological measurements. Depolarization and the impedance characteristics of the epithelium will be more accurate when the surface-scanning electrode is in close proximity to the underlying abnormal epithelium or tumor.

The embodiments described herein are described in reference to humans. However, cancers in non-humans may be also diagnosed with this approach and the present invention is also intended to have veterinary applications.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for determining the condition of an epithelial region of tissue comprising:
   (A) a cup having an interior adapted to receive a volume of fluid, and first and second openings;
   (B) a current-passing electrode disposed within the interior; and
   (C) a source of suction connectable to the first opening; and wherein:
   (i) the first opening is adapted for connection to a source of fluid for introducing the fluid to the cup and alternatively to a source of suction; and
   (ii) the second opening is adapted for placement over a region of tissue; wherein the apparatus is adapted to make an electrical connection between the epithelial region of tissue to be examined and the electrode: (a) upon the application of suction to the first opening to seal the apparatus to a tissue surface: and (b) introduction of fluid to the interior of the cup through the first opening.

2. The apparatus of claim 1, wherein said fluid is physiologic saline solution.

3. The apparatus of claim 1, wherein said source of suction is an aspirator.

4. The apparatus of claim 1, said fluid comprising an electroconductive medium for facilitating an electrical connection between the region of tissue to be examined and the electrode.

5. The apparatus of claim 4, said electroconductive medium comprising a pharmacological challenge agent.

6. The apparatus of claim 1 suitable for measuring impedance of the epithelial region of the tissue.

7. A device adapted to measure electrical properties useful in determining the condition of a region of tissue comprising:
   (A) a housing having an interior space adapted to receive a volume of fluid;
   (B) an electrode positioned within the interior space of the housing;
   (C) said housing including a first opening communicating with the interior space of the housing and adapted to be placed proximate to the surface of a region of tissue; and
   (D) said housing including a second opening adapted to receive suction and communicating with the interior space of the housing.

8. The device of claim 7, further comprising a flange surrounding said first opening.

9. The device of claim 7, wherein the region of tissue comprises ducts.

10. The device of claim 7, wherein the region of tissue is selected from the tissue group consisting of breast, prostate, liver, uterus, pancreas and salivary gland tissue.

11. The device of claim 7 suitable for measuring impedance of the region of tissue.

* * * * *